United States Patent
Ichigaya

(10) Patent No.: US 6,786,273 B2
(45) Date of Patent: Sep. 7, 2004

(54) COOLING SEAT CUSHION

(76) Inventor: Hiroshi Ichigaya, c/o Seft Development Laboratory Co., Ltd. 19-6, Shikatebukuro 6-Chome, Urawa-shi, Saitama 336-0031 (JP)

( * ) Notice: Subject to any disclaimer, the term of this patent is extended or adjusted under 35 U.S.C. 154(b) by 0 days.

(21) Appl. No.: 10/183,541

(22) Filed: Jun. 28, 2002

(65) Prior Publication Data

US 2002/0174972 A1 Nov. 28, 2002

Related U.S. Application Data

(62) Division of application No. 09/830,411, filed on Apr. 27, 2001.

(51) Int. Cl.⁷ .............................. F28F 7/00; F24H 3/02; A47C 31/00; A47C 27/00
(52) U.S. Cl. ...................... 165/46; 165/48.1; 165/121; 297/180.14; 5/423
(58) Field of Search .................. 165/46, 121, 122, 165/48.1, 168, 47; 297/180.11, 180.12, 180.13, 180.14; 5/423

(56) References Cited

U.S. PATENT DOCUMENTS

| | | | |
|---|---|---|---|
| 3,681,797 A | * 8/1972 | Messner | 297/180.13 |
| 3,757,366 A | * 9/1973 | Sacher | 5/423 |
| 4,141,585 A | * 2/1979 | Blackman | 297/180.14 |
| 4,413,857 A | * 11/1983 | Hayashi | 297/180.11 |
| 4,529,248 A | * 7/1985 | Trotman et al. | 297/452.45 |
| 4,821,354 A | * 4/1989 | Little | 5/422 |
| 4,923,248 A | * 5/1990 | Feher | 297/180.11 |
| 5,329,656 A | * 7/1994 | Leggett | 5/709 |
| 5,382,075 A | * 1/1995 | Shih | 297/180.14 |
| 5,452,487 A | * 9/1995 | Leggett | 5/709 |
| 5,692,952 A | * 12/1997 | Chih-Hung | 297/180.11 |
| 5,878,807 A | * 3/1999 | Takahashi | 165/46 |
| 5,954,129 A | * 9/1999 | Takahashi | 165/46 |
| 6,109,688 A | * 8/2000 | Wurz et al. | 297/180.14 |
| 6,189,966 B1 | * 2/2001 | Faust et al. | 297/180.14 |
| 6,263,530 B1 | * 7/2001 | Feher | 5/423 |
| 6,516,624 B1 | 2/2003 | Ichigaya | |

FOREIGN PATENT DOCUMENTS

| | | | |
|---|---|---|---|
| EP | 1 101 429 A1 | | 5/2001 |
| FR | 2 641 956 | | 1/1989 |
| JP | 54-178609 | | 5/1931 |
| JP | 54178609 | * | 12/1979 |
| JP | 07313300 | * | 5/1995 |
| JP | 08056795 | * | 3/1996 |
| JP | 09154669 | * | 6/1997 |

* cited by examiner

Primary Examiner—Henry Bennett
Assistant Examiner—Tho V Duong
(74) Attorney, Agent, or Firm—Rabin & Berdo, PC

(57) ABSTRACT

A seat cushion has cooling flow passages that are provided in a substantially parallel and planar manner. Air at a temperature lower than the body temperature is blown through the cooling flow passages substantially parallelly to the body surface of a person sitting on the cushion. As a result, the temperature gradient near the body surface is increased so as to release heat from the body, resulting in a feeling of coolness.

2 Claims, 19 Drawing Sheets

28°C ⇒

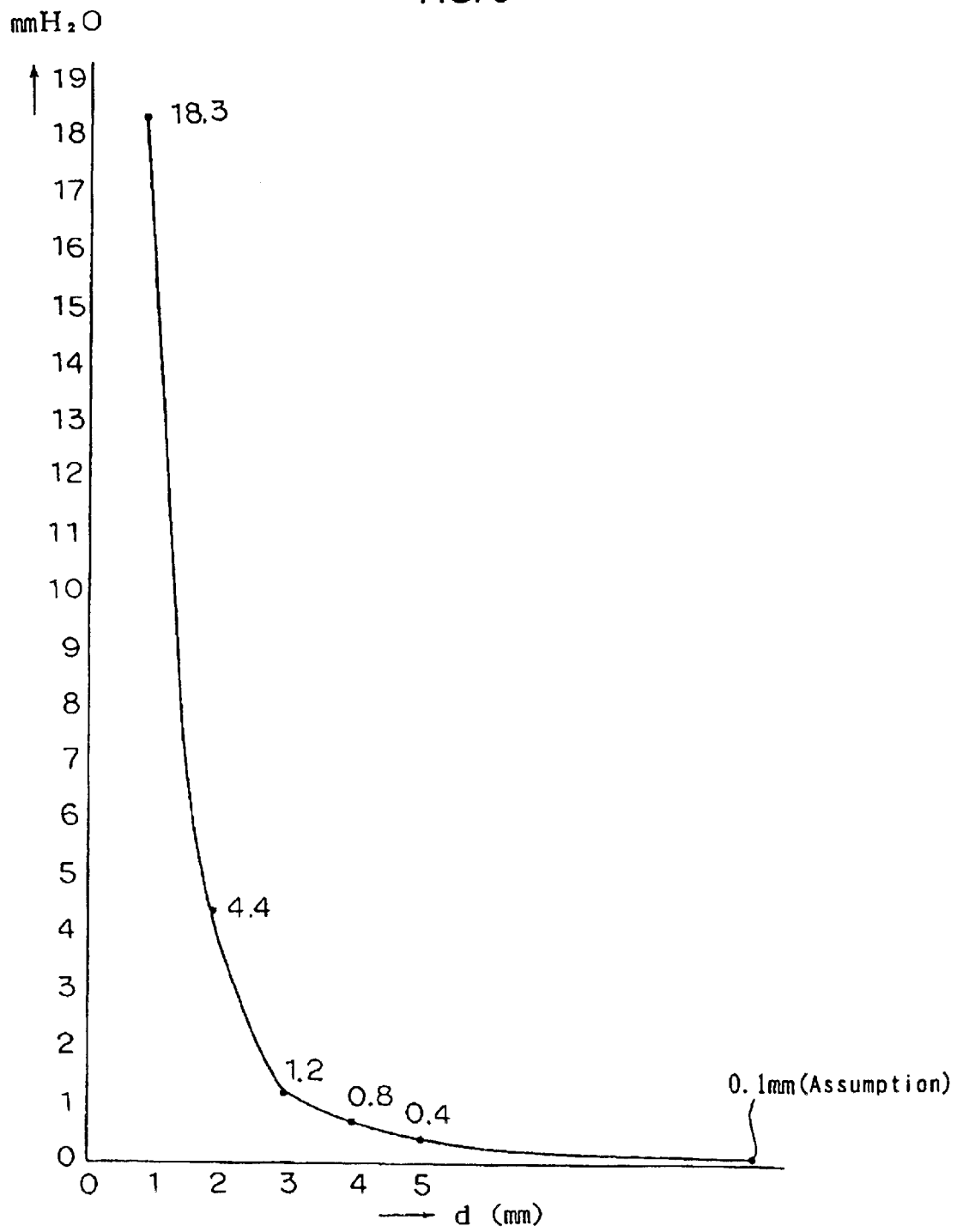

FIG. 4A1
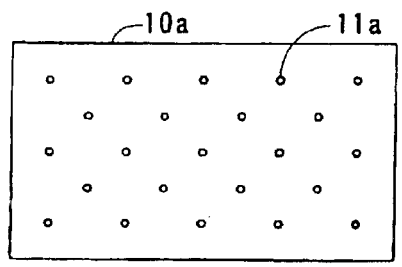
FIG. 4B1
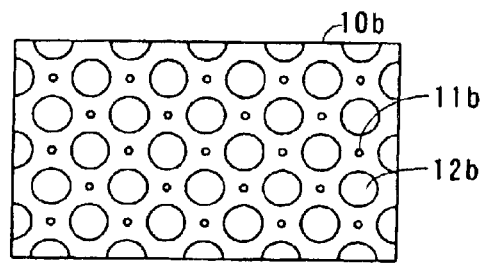
FIG. 4A2
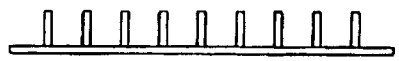
FIG. 4B2
FIG. 4C1
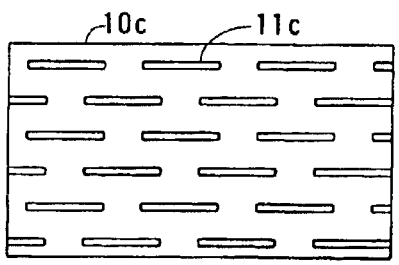
FIG. 4D1
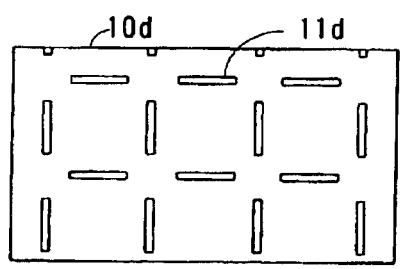
FIG. 4C2
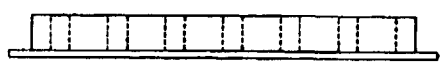
FIG. 4D2
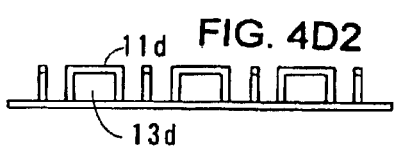
FIG. 4E1
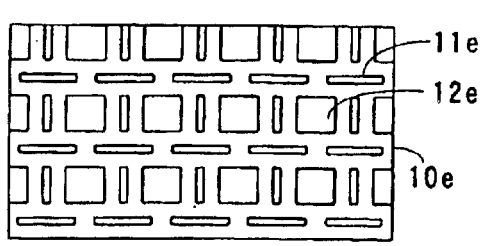
FIG. 4F1
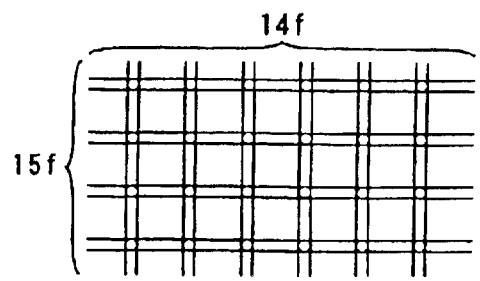
FIG. 4E2
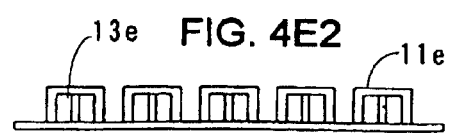
FIG. 4F2

FIG. 5A1
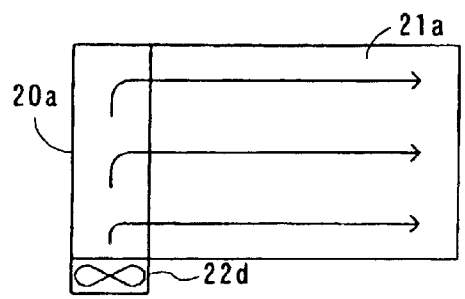
FIG. 5B1
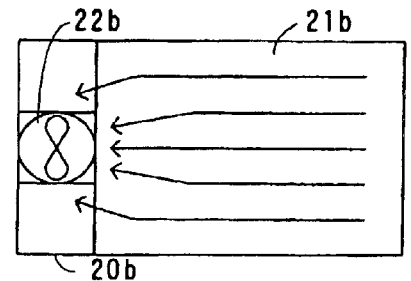
FIG. 5A2
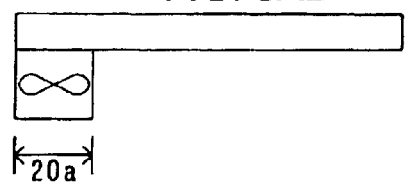
FIG. 5B2
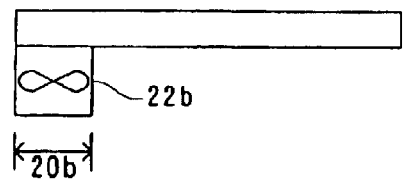
FIG. 5C1
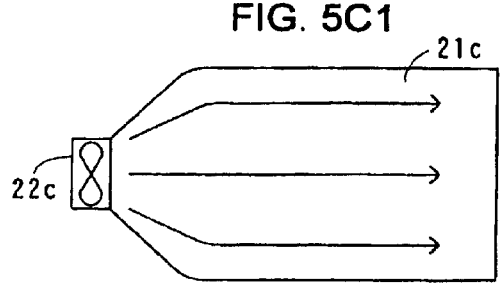
FIG. 5D1
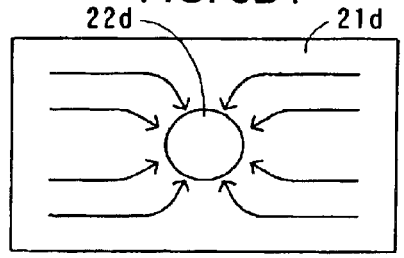
FIG. 5C2
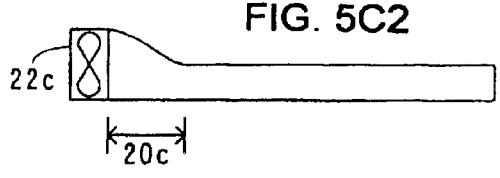
FIG. 5D2
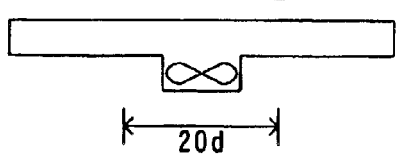

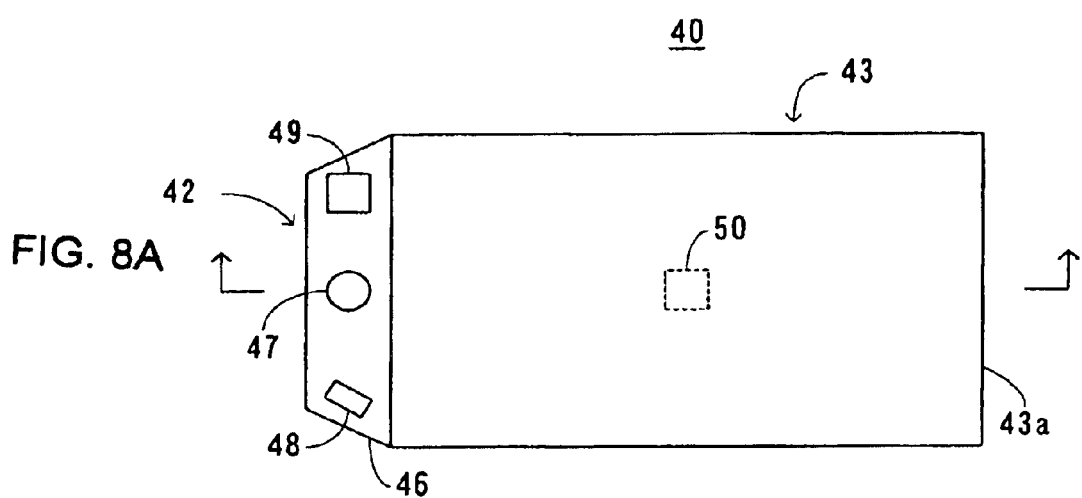
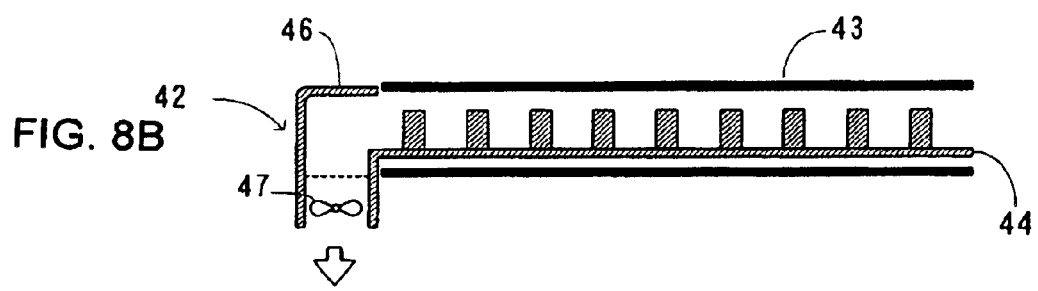

US 6,786,273 B2

COOLING SEAT CUSHION

CROSS REFERENCE TO RELATED APPLICATION

This is a division of application No. 09/830,411, filed Apr. 27, 2001.

TECHNICAL FIELD

The present invention relates to cooling bedclothes, cooling seat cushions, cooling mats, cooling chairs, cooling clothing and cooling shoes, for causing ambient air to flow parallel to and in the vicinity of the body surface thereby to cool the same.

BACKGROUND ART

As bedclothes for cooling a body such as on a sleepless summer night, devices for directly cooling the body have been proposed such as by causing cooled air to flow into a futon and/or pillow. It has been also proposed to directly blow the thus cooled air onto the body such as from small holes provided on a futon and/or pillow.

However, obtaining cooled air requires a separate device therefor, thereby increasing cost. Further, the method to directly blow the cooled air onto the body has a higher cooling effect, but may increase the risk of damage to health.

DISCLOSURE OF INVENTION

The present invention has been carried out in view of such a technical background, and it is therefore an object of the present invention to provide cooling bedclothes, cooling seat cushions, cooling mats, cooling chairs, cooling clothing and cooling shoes, which provide a sufficient cooling effect with a simple structure and without health damage.

To achieve the above object, the first invention resides in a cooling underlying futon comprising: cooling flow passages formed in a substantially parallel and planar manner adjacent to that portion of the futon on an elastic member, which contacts a body of a person; an inlet for drawing air into the cooling flow passages; an outlet for discharging the air from the cooling flow passages; at least one electromotive fan provided at at least one of the inlet and outlet; and a flow connecting passage provided between the electromotive fan and the cooling flow passages; whereby the ambient air at a temperature lower than the body temperature is caused by the electromotive fan to flow through the cooling flow passages substantially parallel to the body surface so as to increase the temperature gradient between the body and the cooling flow passages in order to release the heat emitted from the body to thereby cool the body; and wherein the cooling flow passages are formed from a spacer and a sheet-like material, the sheet-like material being arranged between the spacer and the body and having a thickness of 5 mm or less; and the spacer is formed from a common member and a plurality of physically contiguous subspacers formed on the common member integrally with the same, the subspacers being configured such that the cooling flow passages have a thickness of 3 mm or more.

To achieve the above object, the second invention resides in a cooling seat cushion usable on a seat portion, the cooling seat cushion comprising: cooling flow passages formed in a substantially parallel and planar manner adjacent to that portion of the cooling seat cushion, which contacts a body of a person; an inlet for drawing air into the cooling flow passages; an outlet for discharging the air from the cooling flow passages; at least one electromotive fan provided at at least one of the inlet and outlet; a battery for energizing the electromotive fan; and a flow connecting passage provided between the electromotive fan and the cooling flow passages; whereby the ambient air at a temperature lower than the body temperature is caused by the electromotive fan to flow through the cooling flow passages substantially parallel to the body surface so as to increase the temperature gradient between the body and the cooling flow passages in order to release the heat emitted from the body to thereby cool the body; and wherein the cooling flow passages are formed from a spacer and a sheet-like material, the sheet-like material being arranged between the spacer and the body and having a thickness of 5 mm or less; and the spacer is formed from a common member and a plurality of physically contiguous subspacers formed on the common member integrally with the same, the subspacers being configured such that the cooling flow passages have a thickness of 2 mm or more.

To achieve the above object, the third invention resides in a cooling mat comprising: cooling flow passages formed in a substantially parallel and planar manner adjacent to that portion of the cooling mat, which contacts a body of a person; an inlet for drawing air into the cooling flow passages; an outlet for discharging the air from the cooling flow passages; at least one electromotive fan provided at at least one of the inlet and outlet; and a flow connecting passage provided between the electromotive fan and the cooling flow passages; whereby the ambient air at a temperature lower than the body temperature is caused by the electromotive fan to flow through the cooling flow passages substantially parallel to the body surface so as to increase the temperature gradient between the body and the cooling flow passages in order to release the heat emitted from the body to thereby cool the body; and wherein the cooling flow passages are formed from a spacer and a sheet-like material, the sheet-like material being arranged between the spacer and the body and having a thickness of 5 mm or less; and the spacer is formed from a common member and a plurality of physically contiguous subspacers formed on the common member integrally with the same, the subspacers being configured such that the cooling flow passages have a thickness of 2 mm or more.

To achieve the above object, the fourth invention resides in a cooling chair comprising: cooling flow passages formed in a substantially parallel and planar manner adjacent to that portion of a seat portion of the cooling chair, which contacts a body of a person; an inlet for drawing air into the cooling flow passages; an outlet for discharging the air from the cooling flow passages; at least one electromotive fan provided at at least one of the inlet and outlet; and a flow connecting passage provided between the electromotive fan and the cooling flow passages; whereby the ambient air at a temperature lower than the body temperature is caused by the electromotive fan to flow through the cooling flow passages substantially parallel to the body surface so as to increase the temperature gradient between the body and the cooling flow passages in order to release the heat emitted from the body to thereby cool the body; and wherein the cooling flow passages are formed from a spacer and a sheet-like material, the sheet-like material being arranged between the spacer and the body and having a thickness of 5 mm or less; and the spacer is formed from a common member and a plurality of physically contiguous subspacers formed on the common member integrally with the same, the subspacers being configured such that the cooling flow passages have a thickness of 2 mm or more.

To achieve the above object, the fifth invention resides in a piece of cooling clothing comprising: a plurality of mutually independent cooling flow passages formed in a substantially parallel and planar manner adjacent to that portion of the cooling clothing, which contacts a body of a person; an elastic material for connecting the plurality of cooling flow passage; an inlet for drawing air into the cooling flow passages; an outlet for discharging the air from the cooling flow passages; at least one electromotive fan provided at at least one of the inlet and outlet; and a battery for energizing the electromotive fan; whereby the ambient air at a temperature lower than the body temperature is caused by the electromotive fan to flow through the cooling flow passages substantially parallel to the body surface so as to increase the temperature gradient between the body and the cooling flow passages in order to release the heat emitted from the body to thereby cool the body; and wherein the cooling flow passages are formed from a spacer and a sheet-like material, the sheet-like material being arranged between the spacer and the body and having a thickness of 5 mm or less; and the spacer is formed from a common member and a plurality of physically contiguous subspacers formed on the common member integrally with the same, the subspacers being configured such that the cooling flow passages have a thickness of 2 mm or more.

To achieve the above object, the sixth invention resides in a cooling shoe comprising: cooling flow passages formed in a substantially parallel and planar manner adjacent to that portion of the cooling shoe, which contacts a foot sole of a person; an inlet for drawing air into the cooling flow passages; an outlet for discharging the air from the cooling flow passages; an electromotive fan provided at one of the inlet and outlet; a battery for energizing the electromotive fan; and a flow connecting passage provided between the electromotive fan and the cooling flow passages; whereby the ambient air at a temperature lower than the body temperature is caused by the electromotive fan to flow through the cooling flow passages substantially parallel to the foot sole so as to increase the temperature gradient between the foot sole and the cooling flow passages in order to release the heat emitted from the foot sole to thereby cool the foot sole; and wherein the cooling flow passages are formed from a spacer and a sheet-like material, the sheet-like material being arranged between the spacer and the body and having a thickness of 5 mm or less; and the spacer is formed from a common member and a plurality of physically contiguous subspacers formed on the common member integrally with the same, the subspacers being configured such that the cooling flow passages have a thickness of 2 mm or more.

To achieve the above object, the seventh invention resides in a cooling covering futon comprising: cooling flow passages formed in a substantially parallel and planar manner adjacent to that portion of the cooling covering futon, which contacts a body of a person; an inlet for drawing air into the cooling flow passages; an outlet for discharging the air from the cooling flow passages; at least one electromotive fan provided at at least one of the inlet and outlet; and a flow connecting passage provided between the electromotive fan and the cooling flow passages; whereby the ambient air at a temperature lower than the body temperature is caused by the electromotive fan to flow through the cooling flow passages substantially parallel to the body surface so as to increase the temperature gradient between the body and the cooling flow passages in order to release the heat emitted from the body to thereby cool the body, and wherein the cooling flow passages are formed from a spacer and a sheet-like material, the sheet-like material being arranged between the spacer and the body and having a thickness of 10 mm or less; and the spacer is formed from a common member and a plurality of physically contiguous subspacers formed on the common member integrally with the same, the subspacers being configured such that the cooling flow passages have a thickness of 3 mm or more.

To achieve the above object, the eighth invention resides in a cooling pillow comprising: cooling flow passages formed in a substantially parallel and planar manner adjacent to that portion of the cooling pillow, which contacts a head of a person; a cushioning member for carrying the cooling flow passage thereon; an inlet for drawing air into the cooling flow passages; an outlet for discharging the air from the cooling flow passages; at least one electromotive fan provided at at least one of the inlet and outlet; soundproof means provided for the electromotive fan; and a flow connecting passage provided between the electromotive fan and the cooling flow passages; whereby the ambient air at a temperature lower than the body temperature is caused by the electromotive fan to flow through the cooling flow passages substantially parallel to the head surface so as to increase the temperature gradient between the head and the cooling flow passages in order to release the heat emitted from the head to thereby cool the head; and wherein the cooling flow passages are formed from a spacer and a sheet-like material, the sheet-like material being arranged between the spacer and the body and having a thickness of 5 mm or less; and the spacer is formed from a common member and a plurality of physically contiguous subspacers formed on the common member integrally with the same, the subspacers being configured such that the cooling flow passages have a thickness of 2 mm or more.

BRIEF DESCRIPTION OF DRAWINGS

FIG. 3 is a graph showing a result of a preliminary experiment for testing the relationship between the interspace and pressure in the flow passages while fixing the flow rate of air;

FIGS. 4A1–4F2 are views showing various spacers;

FIGS. 5A1–5D2 are views showing various configurations of flow connecting passages;

FIGS. 8A and 8B are views showing a chair seat cushion according to a second embodiment of the present invention applied to a cooling seat cushion;

BEST MODE FOR CARRYING OUT THE INVENTION

The best mode for carrying out the present invention will be described hereinafter, with reference to the accompanying drawings.

Figure 1A:
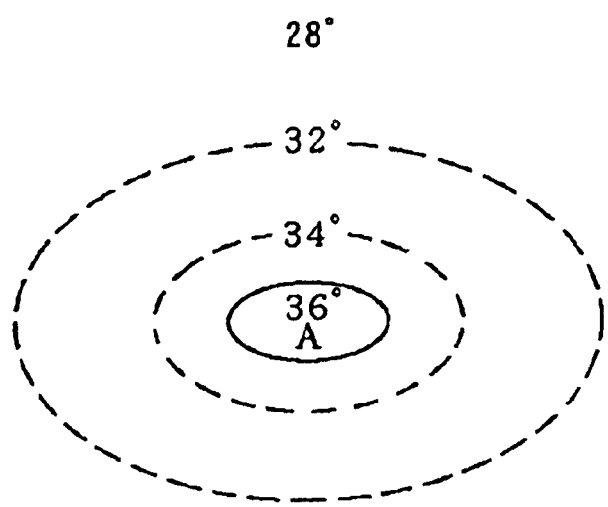
FIGS. 1A, 1B, and 1C are explanatory views of a cooling effect of the present invention.
Figure 1B:
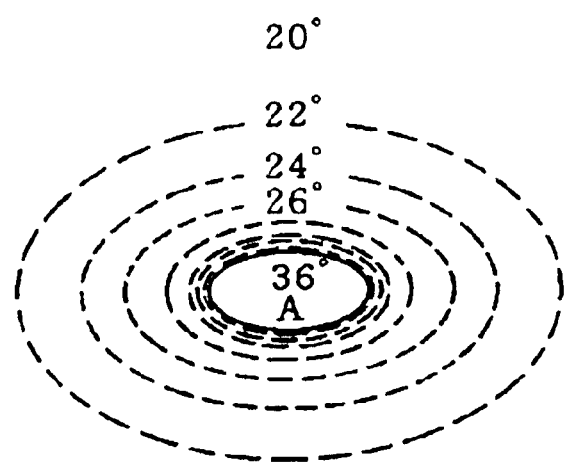
Figure 1C:
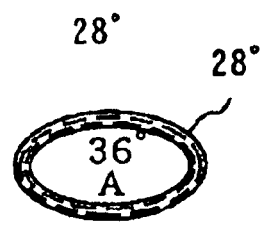

As described hereinafter, the present invention can be applied to articles such as bedclothes, mats, chair seat cushions, chairs, clothing and shoes, all of which are used in a state directly contacting with a body or indirectly adjoining thereto via clothes. The embodiments of the present invention have such a structural feature common to the embodiments disclosed herein to form the cooling flow passages in a substantially parallel and planar manner in the portion of such an article adjacent to the body, and utilize such a common cooling effect common to the embodiments, to cause the ambient air at a temperature lower than the body temperature to flow through the cooling flow passages substantially parallel to the body surface to thereby cool the body. As such, the common cooling effect and FIGS. 1A–1C are explanatory views of a cooling effect of the present invention. FIG. 1A is a schematic view showing a distribution of temperatures by isothermal lines (broken lines) around a person staying in a room inherently at a temperature of 28° C. (which is substantially equal to the temperature in a bedroom on a sleepless midsummer night). Assuming that the body temperature (assumed to be 36° C.) of the person A as a homoiothermal animal is substantially constant and no convection exists within the air of the room, the temperatures of various locations of the room are such that the temperature at the body surface of the person A is 36° C. as the highest, and gradually approaches 28° C. as the distance of a location from the person increases. To the contrary, FIG. 1B is a schematic view showing a distribution of temperatures by isothermal lines around a person staying in a room inherently at a temperature of 20° C.

Comparison of the depictions of FIG. 1A and FIG. 1B shows that the pitches between isothermal lines in FIG. 1B are denser than those in FIG. 1A. In other words, the temperature gradient in FIG. 1B is steeper than that in FIG. 1A. This magnitude of temperature gradient affects the extent of heat release from the person and thus largely affects the temperature feeling of the person, such that the larger the temperature gradient, the more the extent of heat release, thereby providing a cooler feeling to the person.

This is the point at which the present invention has aimed, and thus forms, at a location extremely adjacent to the body surface of a person, an air layer having a temperature equal to that in the room without lowering the temperature of the whole room, thereby forcibly increasing the temperature gradient near the body surface to thereby increase the extent of heat release from the body, resulting in the feeling of coolness. FIG. 1C shows a distribution of temperatures where the person A is located in a room at a temperature of 28° C., and an air layer having a temperature of 28° C. equal to that of the room is formed extremely adjacently to the body of the person A. In this case, the room temperature is 28° C. identically with FIG. 1A. However, since the isothermal line of 28° C. exists extremely adjacently to the body surface of the person A, the temperature gradient in this case is substantially equal to that of the FIG. 1B where the room temperature is 20° C., insofar as concerned with the relationship between the body surface of the person A and the air layer of 28° C. Thus, if it is permitted to form an air layer at the room temperature adjacently to the body surface such as shown in FIG. 1C, the person A will be allowed to feel coolness in the case of the room temperature of 20° C. though the actual room temperature is 28° C. It is of course difficult to actually cause air to flow along the whole of the body surface as shown in FIG. 1C. Nonetheless, if it is permitted to even partially form an air layer at the room temperature adjacently to the body surface, a coolness feeling will be obtained at such a location.

Figure 2:
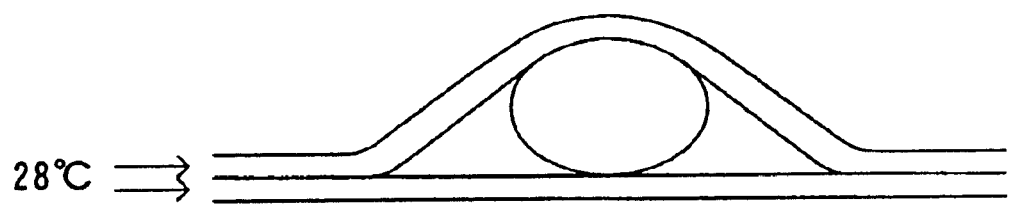
FIG. 2 is a view showing a state where cooling flow passages are formed in the vicinity of a body surface.

The cooling effect according to the present invention will be now considered in more detail. To form an air layer at the room temperature adjacently to the body surface, it is enough to form air flow passages adjacently to the body surface, and to cause the air within the room to flow through the passages parallel to the body surface as shown in FIG. 2. At this time, smaller amounts of air flowing per unit time deteriorate the cooling effect, since the air is warmed before exiting the flow passages. Further, heat from the body is not efficiently released to the air flowing through the cooling flow passages, when the heat resistance (i.e., degree of difficulty in heat conduction) of the body-contacting member of those constituting the cooling flow passages is large.

It is now assumed such an ideal state that the rate of air flow through the cooling flow passages is infinitely large and the heat resistance of the body-contacting member is zero, and the air within a room at a temperature of 28° C. is caused to flow through the flow passages of FIG. 2 under such an ideal state. Then, there is provided such an extreme cooling effect that heat is taken away from the inside of the body so that the surface temperature of the body is brought to a fixed temperature of 28° C. To approach such an ideal state, it is necessary to constitute an air flow having a larger flow rate adjacently to the body surface, and for this purpose, it is advantageous to sufficiently reduce the thickness of the flow passages.

However, the reduced thickness of the cooling flow passages in order to increase the flow rate results in an increased pressure for causing air to flow into the flow passages, mainly due to the viscosity of air. In this respect, FIG. 3 is a graph of the result of a preliminary experiment, showing a transition of a difference between an inlet pressure and an outlet pressure when the inlet and outlet are provided such that: two aluminum plates of 500 mm length and 250 mm width are disposed in parallel to each other, both ends in the longitudinal direction are opened, both side ends are air-tightly closed, and air is supplied in the longitudinal direction at a flow rate of 1 liter/sec by an electromotive fan while changing the distance between the aluminum plates. In FIG. 3, the abscissa represents the distance d [mm] between two aluminum plates, and the ordinate represents the pressure difference p [mmH$_2$O]. Here, the pressure unit [mmH$_2$O] has a relationship with 1 mm such that 1 mmH$_2$O=9.672×10$^{-5}$ atm.

Since the amount of supplied air is fixed, the smaller the distance d, the larger the flow rate of air, as shown in FIG. 3. As the flow rate becomes large, the resistance to which the flowing air is subjected becomes large due to the friction between the air having viscosity and the inner wall of the passage. As such, when the thickness of the cooling flow passage is reduced in order to increase the flow rate, the required pressure is rapidly increased as shown in FIG. 3. Pressures exceeding a certain level require a specific fan, thereby resulting in an excessive cost, larger electric power consumption, and a non-negligible noise problem. Under these circumstances, it is impractical to reduce the thickness of the cooling flow passage down to a value smaller than 2 mm. On the other hand, excessively increased thickness of the cooling flow passage results in a deteriorated cooling effect and an increased strength required for a spacer for forming the cooling flow passage. Thus, the practical upper limit of the thickness is on the order of 20 to 30 mm, depending on the embodiments.

Further, the body-contacting side of the cooling flow passage is formed of a sheet-like member to thereby prevent the air in the flow passage from leaking onto the body surface. In this case, the sheet thickness is limited due to various conditions. Firstly, from the viewpoint to reduce the heat resistance and to bring the cooling flow passage closer to the body, the sheet is preferably as thin as possible. On the other hand, in case that the present invention is applied to such as an underlying futon and a mat, the sheet-like member is preferably formed of a fabric having a certain thickness so as to mitigate a rugged feeling caused by subspacers distributed to form the cooling flow passages. However, the smaller thickness is preferable from the viewpoint of reduced heat resistance. Thus, the upper limit of the thickness of the sheet-like member is on the order of 5 mm.

Meanwhile, when the sheet of the body-contacting side of the cooling flow passage is formed of fabric, the moisture content evaporated from the body permeates the sheet to reach the cooling flow passage side, and the moisture content is carried away to the outside by the air flowing through the passage. Thus, there can be expected such a side effect that an uncomfortable sweaty condition due to perspiration can be avoided.

There will be now described the relationship between the amount of air supplied through the cooling flow passage, and the absorbed heat amount. The experiment conducted by the group including the present inventor concerning an underlying futon showed that the averaged temperature of exhausted air was approximately 30° C. when the air of a room at a temperature of 27° C. was supplied at a rate of 5 liter/sec through an underlying futon of an air flow-through type on which a person was lying. The heat amount required to raise the temperature of 1 liter of air by 1° C. is approximately 0.3 calories. Thus, when the air is kept supplied for 1 hour under the above condition, the heat amount of approximately 16.2 kilocalories will be absorbed from the body. Further, also considering the evaporation heat to be absorbed from the surroundings when perspiration evaporates, the heat absorbing effect of the aforementioned extent ensures a sufficiently comfortable sleep in a room even at a temperature of 27° C. Moreover, when the amount of air to be supplied is on the order of 5 liter/sec, an axial fan of about 60 square (60 mm×60 mm) will do.

Next, there will be described general matters that are in common among the embodiments to be described later, concerning a spacer for forming the cooling flow passage adjacently to the body surface. The spacer is required to form the cooling flow passage, and will have varying strength depending on the situation of a covering futon which will not receive a relatively large load, an underlying futon which can bear a large load so as to support a person's body, or a pillow to be classified between them. In all of the present embodiments, there is used a planar spacer comprising a plate-like member and subspacers integrally formed on the plate-like member. Such a planar spacer can be economically manufactured such as by injection molding of soft plastic or forming of rubber.

Each of FIG. 4A1 through FIG. 4F1 shows a view of a part of each of various spacers to be used in the embodiments to be described later, by a plan view and a lateral view shown in the upper and lower sides of each figure, respectively. In the following, the planar spacers (a) through (f) shall be referred to as "a-type" through "f-type", respectively.

In the Figures, the a-type planar spacer comprises a plate-like member 10a as a common member, and subspacers 11a in the shape of elongated rod-like projections formed on the plate-like member 10a. Thus, the subspacers 11a and plate-like member 10a can be integrally formed at the same time. This aspect is common to each type described below. Although the planar spacer of the b-type has subspacers 11b having structures the same as those of (a), the plate-like member 10b on which the subspacers are formed is formed with a lot of holes 12b. In this way, the weight of the planar spacer is reduced, and the flexibility thereof is also increased. In the c-type planar spacer, the subspacers 11c formed on the plate-like member 10c are formed as plate-like projections, and arranged such that the longitudinal direction of the subspacer coincides with the lateral direction of the spacer.

In the d-type planar spacer, the longitudinal direction of some of the subspacers 11d formed as plate-like projections is oriented in the lateral direction of the spacer, and the others are oriented in the longitudinal direction. In this type of planar spacer, the respective plate-like subspacers are formed with holes 13d as shown in the associated lower figure. In this way, the flow of air is improved, and the weight reduction and the flexibility improvement are achieved. Also in the e-type planar spacer, the longitudinal direction of some of the subspacers 11e, formed as plate-like projections, is oriented in the lateral direction of the spacer, and the others are oriented in the longitudinal direction, and the respective subspacers 11e are provided with associated holes 13e. Further, a lot of holes 12e are provided between subspacers. In this way, the weight of the planar spacer is further reduced, and its flexibility is increased. The f-type planar spacer has a structure different from those of the a-type through e-type where the subspacers are arranged in a certain pattern on the plate-like member. Namely, the f-type spacer has a structure provided with upper longitudinal rails 14f and lower lateral rails 15f, as well as short rod-like members 16f provided at intersections between the upper and lower rails 14f and 15f to interconnect them. This f-type has such a feature that the inherent function is maintained even when the spacer is turned upside down. Further, it is typical for the planar spacers of the a-type through e-type where the subspacers are arranged on the plate-like member, to be arranged on the plate-like member such as 10a at an underside, and the human body is placed on the tip ends of the projections. However, concerning the planar spacers of the b-type and e-type, the planar spacers can be used in an upside-down reversed manner, since the plate-like member such as 10b or 10e is formed with the large holes 12b or 12e.

Among the aforementioned respective types of planar spacers, those planar spacers of the a-type, b-type and f-type are suitable for embodiments where a smaller load is applied. To the contrary, the planar spacers of the c-type, d-type and e-type are capable of bearing a relatively large load. The most flexible and lightest one is the f-type, and the b-type and e-type will follow it. It is preferable to determine which type of spacer is to be used correspondingly to an applied embodiment, in view of the aforementioned characteristics.

The planar spacer to be used need not be integral as a whole, and such a situation where the planar spacer is divided into a plurality of pieces is of course included within the technical scope of the present invention. Further, in case of usage such as for an underlying futon, it is possible to interpose a mesh-like material between the body-contacting side sheet and the subspacers so as to effectively restrict the rugged feeling caused by the subspacers.

In each of the aforementioned planar spacers, the design as to the arrangement density of subspacers and the distances between subspacers shall be determined such as in view of the strength of material to be used, the shape of the subspacers, and the applicability of embodiment. The important point is to reduce the viscous resistance when the flowing air strikes the subspacers. Larger viscous resistances require a large sized fan for generating a larger pressure, thereby causing a problem of increased power consumption and noise occurrence. Experiment showed a considerable increase in viscous resistance when the distances between the subspacers are smaller than 3 mm and the amount of blown air within a practical range is supplied. Thus, such distances between subspacers and arrangement thereof are desirably designed so that any location on the planar spacer always has a portion having a gap larger than 2 mm as viewed from such a location, and air is allowed to flow out through the gap.

There will be described hereinafter a "flow connecting passage". The installing position of a fan is either of the inlet side or the outlet side of the cooling flow passage (the fan is rotated in a direction to draw the ambient air and blow it toward the cooling flow passage in case of installation at the inlet side, and rotated in another direction to draw the air from the cooling flow passage and blow it toward the surroundings in case of installation at the outlet side). In adopting a fan, and particularly when the fan is to be used for an object having a larger surface area such as an underlying futon, a covering futon or a mat, an axial fan is desirably adopted in view of the subjects of the amount of blown air, power consumption and noise. From an economic viewpoint, it is desirable to provide a single fan having sufficient power rather than a plurality of small fans having smaller amounts of power, or to restrict the number of fans to a few. In that case, the diameter of the fan notably exceeds the thickness of the cooling flow passage. To the contrary, the width of the cooling flow passage is notably larger than the diameter of the fan. Thus, there is required a space for smoothly connecting the fan side and the cooling flow passage side, therebetween. This space is herein referred to as a "flow connecting passage".

FIGS. 5A1 through 5D2 show various configurations of the flow-connecting portion in the upper-side plan views and lower-side lateral cross-sectional views, respectively. In these Figures, the arrows indicate the flowing manner of air. In FIGS. 5A1 and 5A2, a flow connecting passage 20a is provided at the left side of a cooling flow passage 21a. Fan 22a provided at the lower end portion of the flow connecting passage 20a is rotated in a direction to suck air from the surroundings and to feed the air toward the flow connecting passage 20a. The flow direction of the air is changed by 90 degrees at a portion connecting the flow connecting passage and the cooling flow passage, so that the air flows from the left toward the right in the cooling flow passage 21b. In FIGS. 5B1 and 5B2, a fan 22b is provided at the center of the flow connecting passage 20b provided at the left side of the cooling flow passage 21b. This fan 22b is rotated in a direction to suck air from the cooling flow passage 21b and flow connecting passage 20b, and to discharge the air outwardly.

In FIGS. 5C1 and 5C2, a flow connecting passage 20c is provided at the left side of a cooling flow passage 21c. Flow connecting passage 20c has a width increasing from the fan 22c toward the cooling flow passage 21c. FIGS. 5D1 and 5D2 show an example where a fan 22a is provided at the center of a cooling flow passage 21d. As shown in FIGS. 5D1 and 5D2, the fan 22d may be provided at a bottom portion at the center of the cooling flow passage or at a bottom portion closer to the center from the end portion, when the diameter of the fan 22d is not so large as compared to that of the thickness of the passage 21d. The rotational direction of the fan in this case is to suck air from the cooling flow passage and to discharge it downwardly. In the configuration as shown in FIGS. 5D1 and 5D2, those portions around the fan 22d can be regarded as a flow connecting passage 20d.

Figure 6:
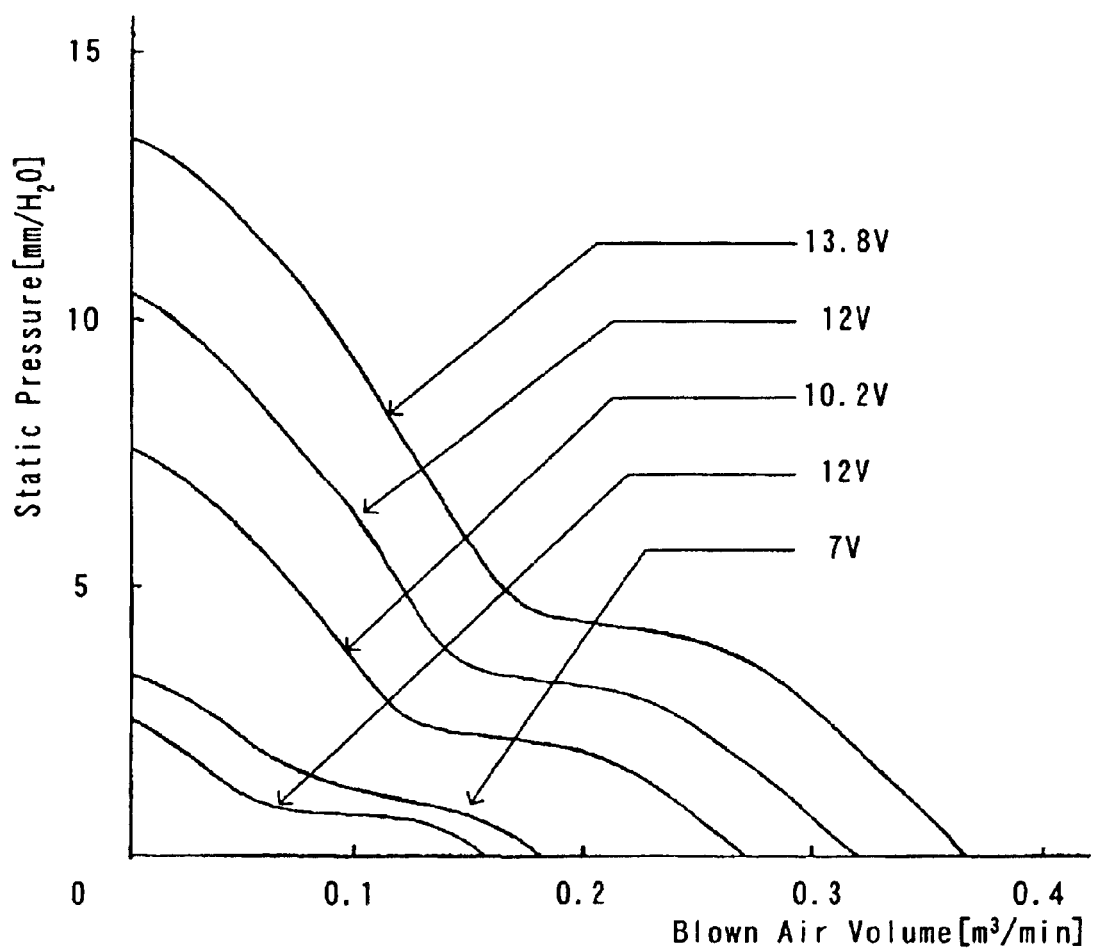
FIG. 6 is a graph showing characteristics of a certain electromotive fan.

There will be now described a relationship between a blown air volume and a static pressure, in a fan for blowing the ambient air through the cooling flow passage. FIG. 6 shows a graph having an abscissa representing a blown air volume at a unit of $m^3/min$ and an ordinate representing a static pressure at a unit of $mmH_2O$, concerning an electromotive fan 109P0412H302 (40 square, and 28 mm thickness) manufactured by SANYO DENKI. Note, the blown air volume of 0.3 $m^3$/min based on the abscissa corresponds to a blown air volume of 5 liter/sec.

As shown in FIG. 6, the higher the voltage applied to the fan, the larger the static pressure and the blown air volume. However, increased voltage possibly leads to a proportionally higher noise level, thereby hindering a calm sleep in case of usage such as in bedclothes. Thus, in case of usage such as in bedclothes and mat, the supplied voltage and the static pressure are desirably restricted to levels of 12 V and 3 $mmH_2O$ or less, respectively. Further, in case of usage in articles such as clothes, shoes, seat cushion, and chair other than the above, the static pressure is desirably 5 $mmH_2O$ or less.

Note, the expression "pressure of fan" used herein shall mean a pressure difference between the ambient pressure in a room and a pressure within a flow connecting passage.

There will be described hereinafter detailed embodiments in which the present invention is applied to various concrete articles.

Embodiment 1

Figure 7A:
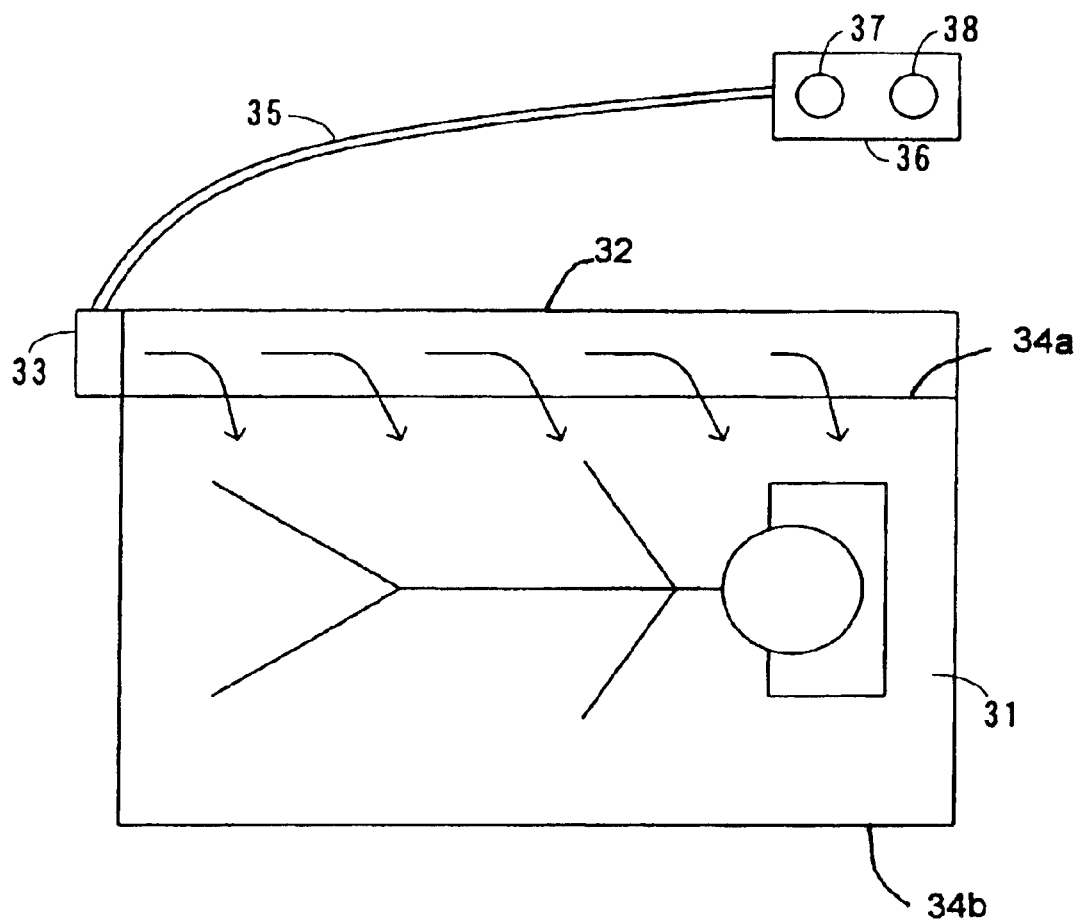
FIGS. 7A and 7B are views showing an underlying futon according to a first embodiment of the present invention applied to cooling bedclothes.
Figure 7B:
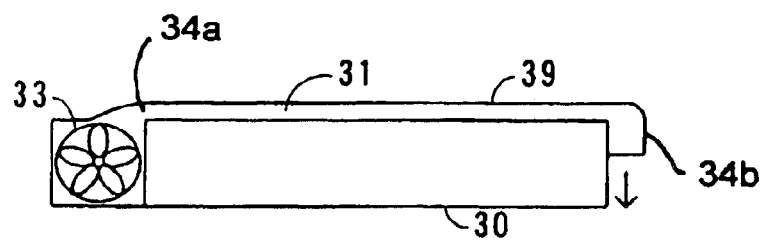

FIGS. 7A and 7B are views showing an underlying futon according to a first embodiment of the present invention applied to cooling bedclothes. FIG. 7A is a plan view and FIG. 7B is a left side view of the cooling bedclothes. The cooling bedclothes of this embodiment have a structure comprising cooling flow passages, or a collective cooling flow passage 31 placed on a cushion 30. As shown in FIG.

7A, a flow connecting passage 32 is provided at the right side of a supine person, and a fan 33 of 60 square is provided at the end of the flow connecting passage 32 adjacent to the feet of the person. The cooling flow passage 31 has a lateral side constituting an air inlet 34a at which the flow connecting passage 32 is provided (i.e., the right side of the lying person), and the other lateral side constituting an air outlet 34b. As shown in FIG. 7B, the air outlet 34b is provided to face downwardly at the side of the cushion. This is to avoid a situation where the air outlet is closed such as by a covering futon. The fan 33 is provided to come close to the feet of the lying person, in view of a noise problem. When the present invention is to be applied to bedclothes such as in this embodiment, it is desirable to adopt an axial fan such as in view of a smaller noise, ensurance of required blown air volume, and reduction of air leakage from a fabric sheet.

Connected to the fan 33 is a controlling part 36 via cord 35. This controlling part 36 is provided with a switchable volume 37 and a timer 38. The switchable volume 37 is provided for switching on/off the operation of the fan, and for adjusting a blown air volume by varying a rotational speed of the fan. The timer 38 may be arbitrarily used by the lying person, or may be arranged such that the fan 33 is automatically stopped or the amount of blown air thereof is automatically reduced after an operation over a predetermined period of time of the fan 33, to thereby avoid overcooling.

In this embodiment, the c-type of planar spacer of FIGS. 4C1 and 4C2 is adopted as the cooling flow passage 31. In this case, the longitudinal direction of the subspacers 11c is arranged in the widthwise direction of the underlying futon, in view of the air-flow direction. The upper side of this spacer is covered by a fabric or cloth 39, and the head side and foot side of the fabric 39 are bonded to the corresponding sides of the planar spacer. In this way, the ambient air drawn by the fan 33 flows through the flow connecting passage 32, enters the cooling flow passage 31, and thereafter flows from the left side toward the right side of the lying person. At this time, there is formed an air layer having a temperature that is the same as that of the ambient air at the vicinity of the lying person's back, thereby increasing the temperature gradient at this portion so that the lying person will feel coolness.

Meanwhile, even when a high-density fabric (woven with about 300 threads per 1 cm) is adopted as the fabric 39, its overall surface area is large so that excessively high pressures at the portion just after the fan 33, i.e., at the flow connecting passage 32, lead to a problem of substantial leakage of air on its way. Further, excessively high pressures also lead to a considerable noise problem. As such, the larger thickness of the cooling flow passage 31 is advantageous so as to ensure a sufficient blown air volume on the order of 5 liter/sec even at a lower pressure. For example, when the thickness of the cooling flow passage is on the order of 10 mm to 15 mm, there can be ensured a sufficient amount of blown air at a lower pressure. Only, the thickness of the cooling flow passage 31 may be reduced down to the order of 3 mm, such as when the blown air volume is reduced to a certain extent, the noise countermeasure is enhanced, or a fabric having a higher thread density, resistant to higher pressures, is adopted. Even when the thickness of the cooling flow passage 31 is reduced in such a way, the pressure within the flow connecting passage just after the fan 33 has a limit of 5 mmH$_2$O.

Embodiment 2

Figure 9:
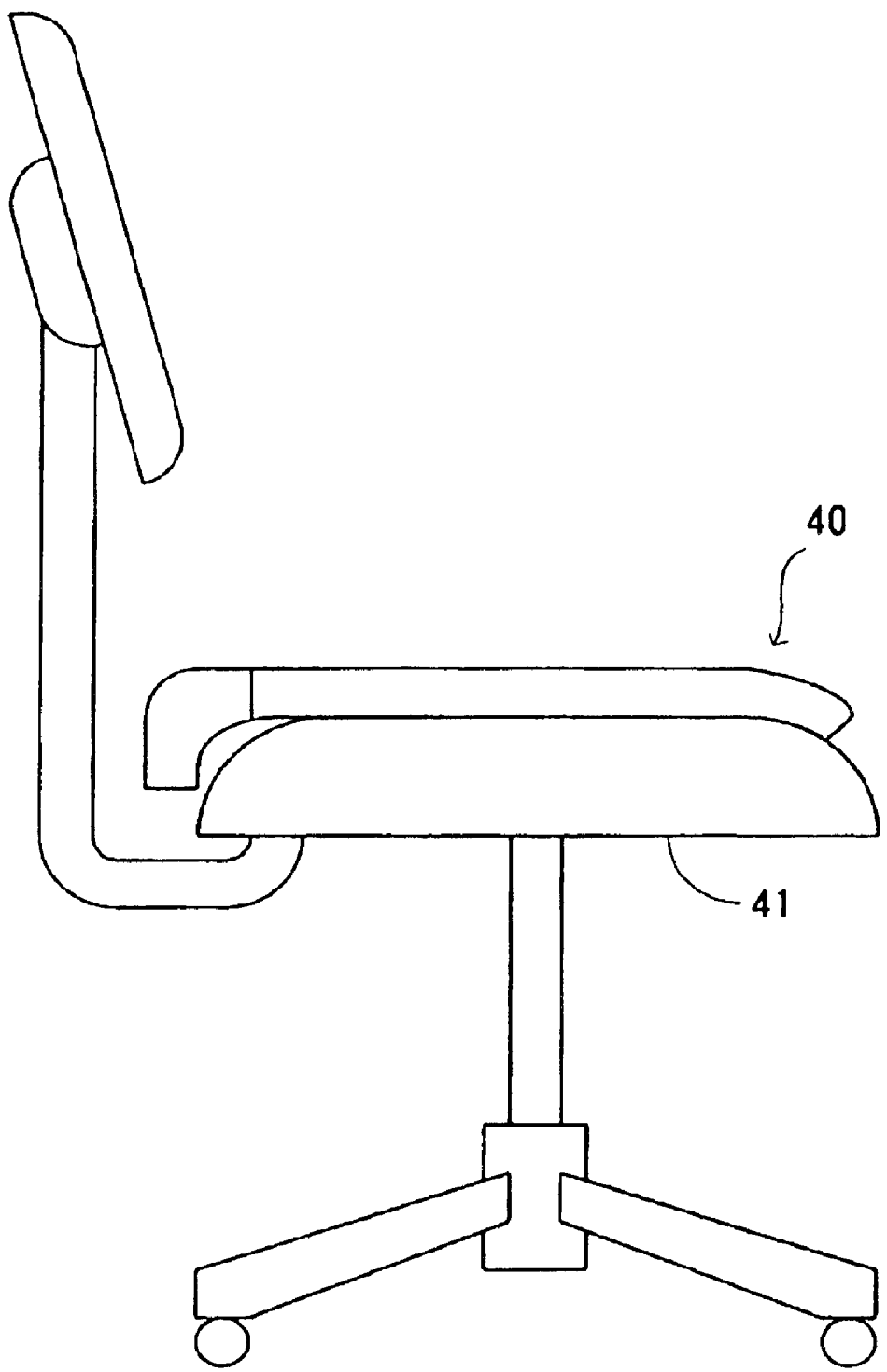
FIG. 9 is a view showing a state where the chair seat cushion is placed on a chair.

FIGS. 8A and 8B are views showing a chair seat cushion according to a second embodiment of the present invention applied to a cooling seat cushion. FIG. 8A is a plan view and FIG. 8B is a center cross-sectional view of the cooling seat cushion. FIG. 9 is a view showing the chair seat cushion according to the second embodiment of the present invention applied to the cooling seat cushion.

Cooling seat cushion 40 of this embodiment is used in a manner placed on a chair 41 as shown in FIG. 9. The cooling seat cushion can be of course placed such as on a bench or sofa. The cooling seat cushion 40 of this embodiment basically constituted of two portions, i.e., a main portion 42 and a seat 43. The main portion 42 comprises a square spacer portion 44 of 400 mm length and 400 mm width, and a controlling part 46 provided at the rear side of the spacer portion 44. The spacer portion 44 has a top side provided with many projected subspacers. The main portion 42 comprising the spacer portion 44 and controlling part 46 is manufactured integrally by injection molding soft plastic. In view of the usage of the cushion to be placed on a chair, its entire size is limited to a length of approximately 500 mm and a width of approximately 500 mm.

Here, the e-type of FIGS. 4E1 and 4E2 is adopted as the configuration of the spacer portion 44. Reduced thickness of the cooling flow passage leads to an increased flow rate to thereby enhance a cooling effect. However, extreme reduction is not practical in view of consumption of a battery, so that the lower limit of the cooling flow passage is on the order of 2 mm.

The seat 43 is in the shape of bag to cover the whole of the spacer portion 44 except the controlling part 46. Only, the right side 43a in FIGS. 8A and 8B is left open to thereby suck air. Any material can be used for the seat 43 if water vapor readily permeates through it, such as the aforementioned high-density fabric or a general fabric.

The controlling part 46 is provided with a DC fan 47 of 40 square, a switch 48, and a battery 49. Although the battery 49 may be a normal dry cell, but it is preferably a rechargeable secondary battery such that it is recharged by the primary power source while the cooling seat cushion is not used. Pressure switch 50 is provided near the center of the main portion 42. The switch 48 and pressure switch 50 are connected in series such that the power from the battery is supplied to the DC fan 47 when both switches are turned on. The portion, where the controlling part 46 is provided, also acts as a flow connecting passage between the DC fan 47 and the cooling flow passage.

When the cooling seat cushion 40 is to be used, it is placed such that the controlling part 46 is brought to the rear portion (at the backrest side) as shown in FIG. 9. Normally, the blowing outlet of the DC fan 47 is placed to face downwardly. However, the cooling seat cushion may be used in an upside-down manner, depending on the structure of an applicable chair. When a person sits on the chair 41 in the above condition, the sensor such as pressure switch 50 for detecting the seating is turned on. When the switch 48 is further turned on, the DC fan 47 rotates in a direction to suck the ambient air through the right side 43a of the seat 43. The air sucked through the side 43a flows through the cooling flow passage formed by the spacer portion 44, and is then exhausted downwardly by the DC fan 47. The amount of air to be flown may be on the order of 1 liter/sec, which can be provided by a small fan such as 40 square.

When a person sits on the chair, the ambient air at a temperature lower than the body temperature is caused to flow just below the buttocks to thereby increase the temperature gradient at the buttocks of the sitting person. Thus, even when the person keeps sitting for a long time, the portion of the seat cushion contacting the buttocks will be never warmed by the body temperature, resulting in comfortable feeling. Since the e-type of spacer having many holes at the bottom plate has been used in this embodiment, a sufficient cooling effect can be obtained even when the cooling seat cushion is used in an upside down manner.

Embodiment 3

Figure 10A:
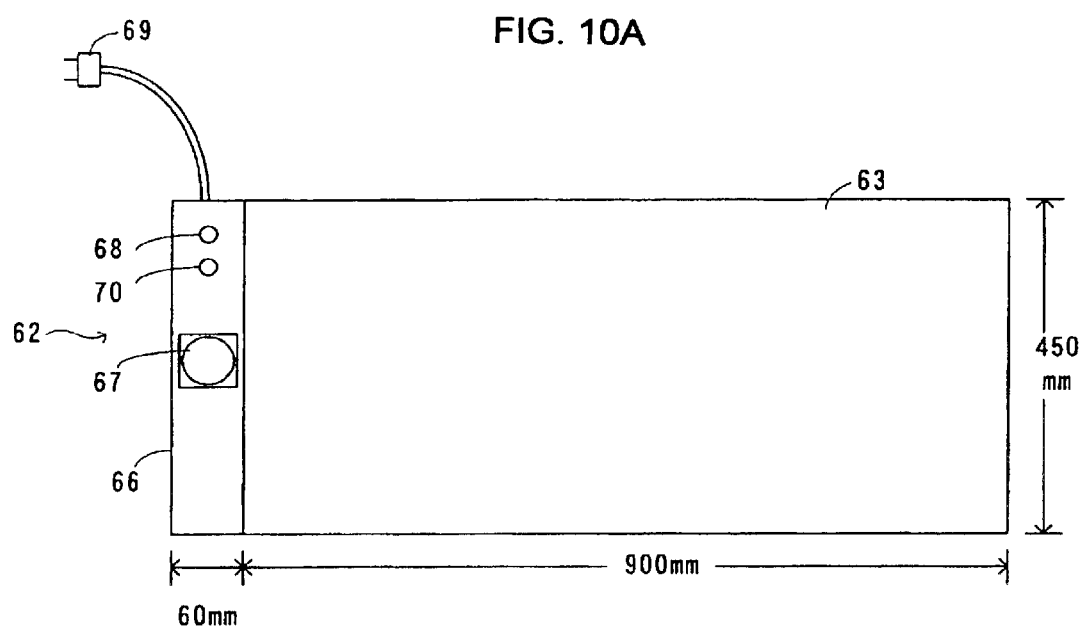
FIGS. 10A and 10B are views showing a mat such as usable on a sofa or floor according to a third embodiment of the present invention applied to a cooling mat.
Figure 10B:
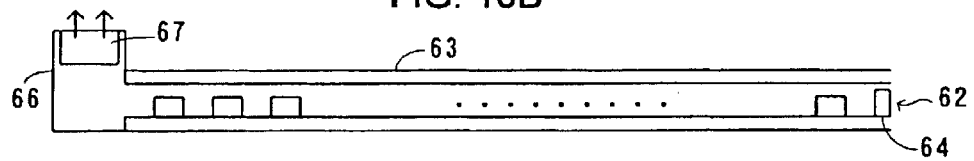

FIGS. 10A and 10B are views showing a mat such as usable on a sofa or floor according to a third embodiment of the present invention applied to a cooling mat. FIG. 10A is a plan view and FIG. 10B is a cross-sectional view of the cooling mat, and FIG. 11 is a view showing which portion of a body is cooled by the mat.

Figure 11:
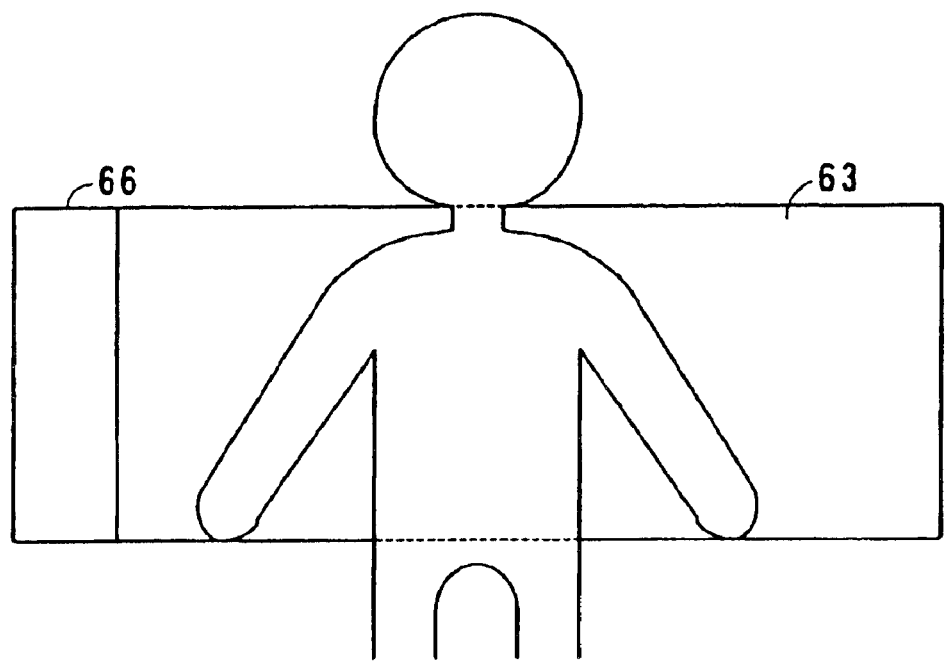
FIG. 11 is a view showing which portion of a body is cooled by the mat of the third embodiment.

Cooling mat of this embodiment is used in a manner to mainly cool the upper half of the body when a person rests such as on a floor or sofa as shown in FIG. 11. The basic structure of the cooling mat of this embodiment basically comprises two portions, i.e., a main portion 62 and a seat 63, similarly to the cooling seat cushion according to the Embodiment 2. The main portion 62 comprises a rectangular spacer portion 64 of 900 mm length and 450 mm width, many subspacers provided on the top side of the spacer portion 64, and a controlling part 66 provided at the rear side of the spacer portion 64. These portions are integrally manufactured by injection molding soft plastic.

As the spacer portion 64, the e-type of FIGS. 4E1 and 4E2 is adopted. The thickness of the cooling flow passage is in a range between 2 mm to 30 mm from the same reason with the aforementioned cooling seat cushion, and approximately 6 mm is suitable.

The seat 63 is in the shape of bag to cover the whole of the spacer portion 64 except the controlling part 66. Only, the right side in FIGS. 10A and 10B is left open to thereby suck air. Any material can be used for the seat 63 if water vapor readily permeates through it, such as the aforementioned high-density fabric or a general fabric.

The controlling part 66 is provided with a fan 67 of 50 square, a switchable volume 68, a plug 69 to be connected to the primary power source, and a timer 70. The controlling part 66 also acts as a flow connecting passage between the fan 67 and the cooling flow passage. The timer 70 may be arbitrarily used by the lying person, or may be arranged such that the fan 33 is automatically stopped or the amount of blown air thereof is automatically reduced after an operation over a predetermined period of time of the fan, to thereby avoid overcooling.

When the cooling mat is to be used, it is placed under the upper half of the body on a floor or on a sofa, as shown in FIG. 11. Normally, the blowing outlet of the fan 67 is placed to face upwardly. However, the cooling mat may be used in an upside-down manner, when used such as on a bed. When the switchable volume 68 is turned on, the fan 67 rotates in a direction to suck the ambient air through the right side of the seat 63. The air sucked through the side flows through the cooling flow passage formed by the spacer portion 64, and is then exhausted upwardly by the fan 67. The amount of air to be flown may be on the order of 3 liter/sec, which can be sufficiently conducted by a small fan such as 50 square.

When a person lies on the cooling mat, the ambient air at a temperature lower than the body temperature is caused to flow such as just below the back and belly of the person to thereby increase the temperature gradient near the back and belly. Thus, even when the person keeps lying for a long time, the mat will be never warmed by the body temperature, resulting in comfortable feeling. Since the e-type of spacer having many holes at the bottom plate has been used in this embodiment, a sufficient cooling effect can be obtained even when the cooling mat is used in an upside down manner.

Embodiment 4

Figure 12:
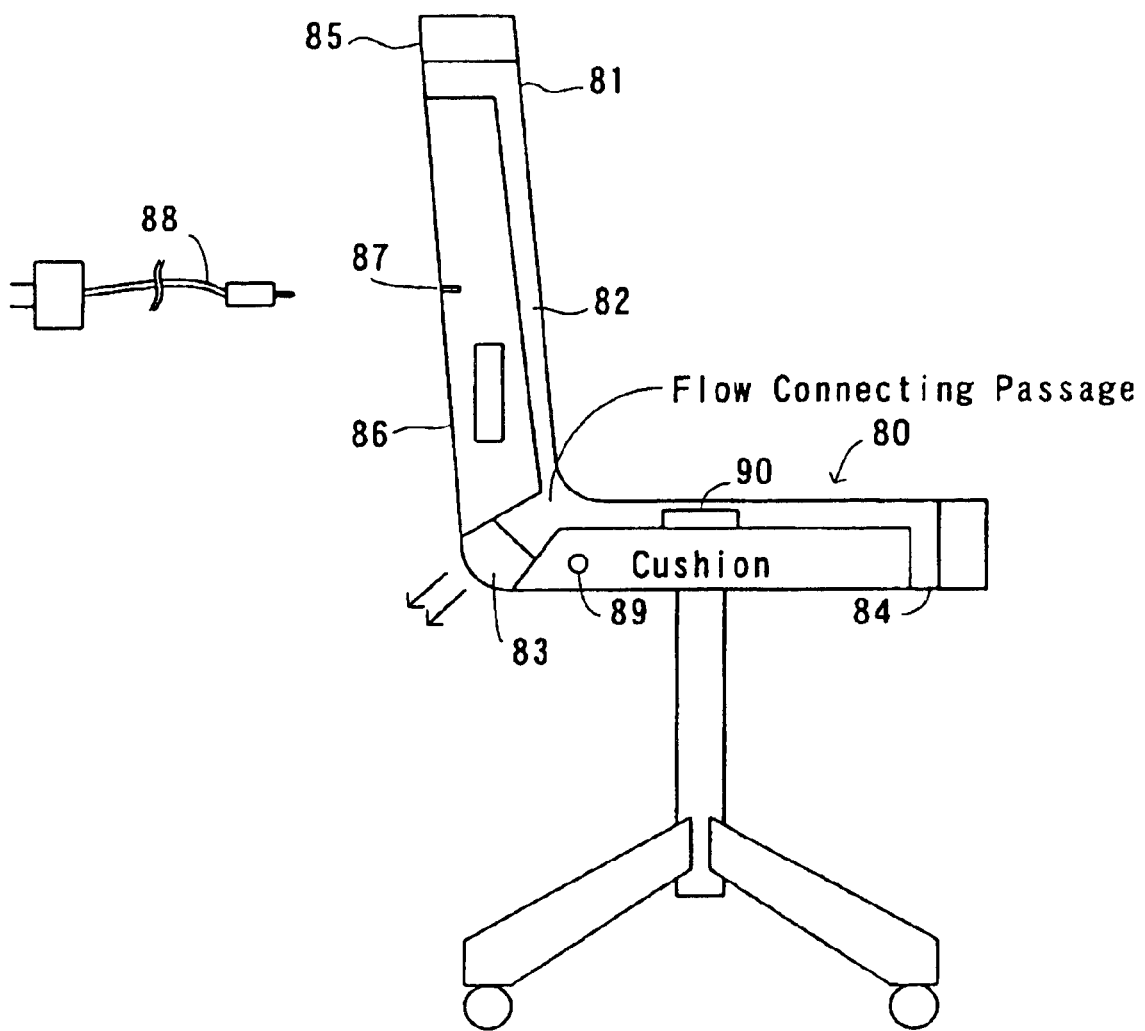
FIG. 12 is a cross-sectional view of a chair according to a fourth embodiment of the present invention applied to a cooling chair.
Figure 13:
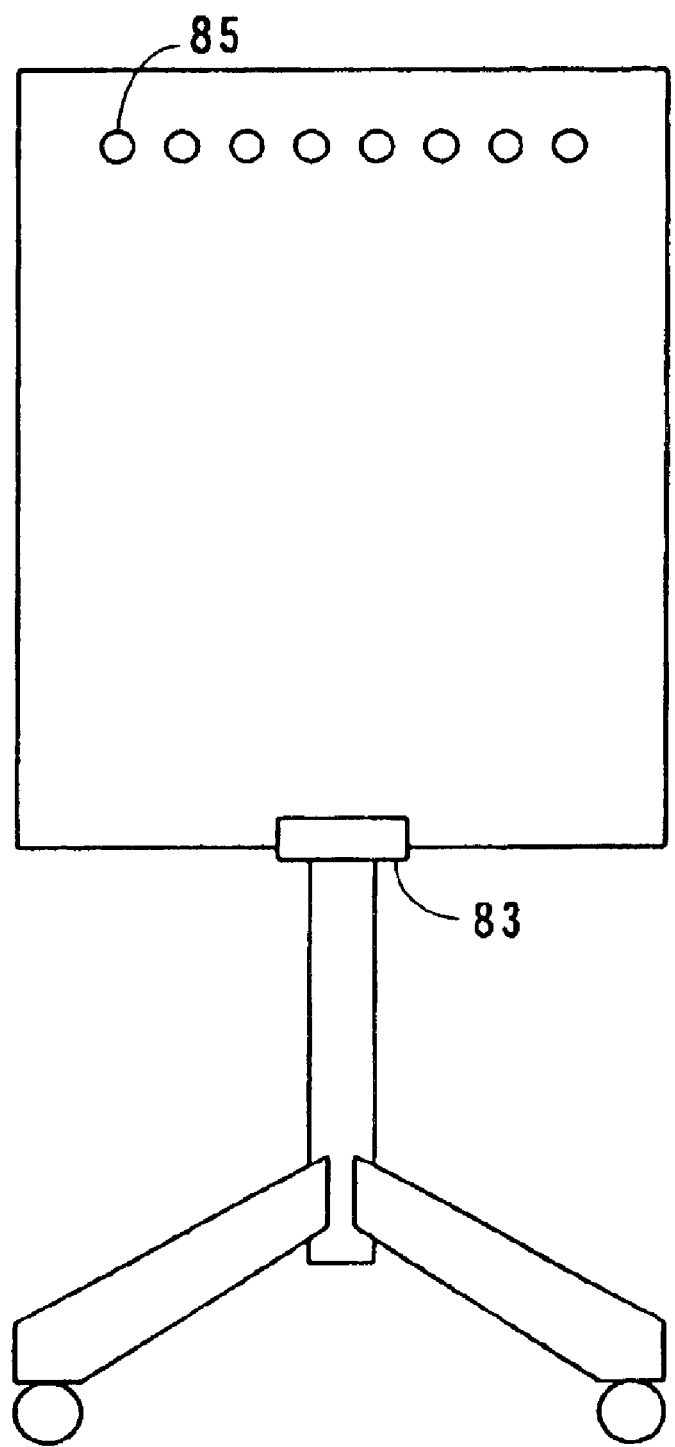
FIG. 13 is a rear view of the cooling chair of the fourth embodiment.

FIG. 12 is a cross-sectional view of a chair according to a fourth embodiment of the present invention applied to a cooling chair, and FIG. 13 is a rear view of the cooling chair.

As shown in FIG. 12, the cooling chair of this embodiment includes a cooling flow passage 82 formed within a seat portion 80 and within a backrest 81. At the area where the seat portion 80 and backrest 81 are interconnected, there is provided a DC fan 83 of 50 square adapted to rotate in a direction to outwardly discharge the air within the portions 80, 81. The blown air volume is suitably on the order of 2 liter/sec under a normal operating state. Provided at the front bottom portion of the seat portion 80 is an air inlet 84, and so is an inlet 85 at the upper rear portion of the backrest 81. The provision of the air inlet 84 at the front bottom portion of the seat portion 80 is to avoid occlusion of the air inlet 84 such as by feet and/or clothes.

The cooling flow passage 82 is provided on the cushions for the seat portion 80 and backrest 81, so that a person sitting on the chair will feel suitable elasticity. In the cooling chair of this embodiment, the c-type of spacer in FIGS. 4C1 and 4C2 is adopted to bear the load on the order of a body weight of a sitting person. Excessively reduced thickness of the cooling flow passage 82 leads to an increased pressure resulting in a larger amount of consumption of a battery 86. Thus, approximately 2 mm is the limit of the thickness. Further, thicknesses of the cooling flow passage exceeding 30 mm are impractical, in view of the cooling principle of this method. Practically, approximately 5 mm is suitable.

The battery 86 for energizing the DC fan 83 is provided within the backrest 81 at the rear side of the seat portion 80. This battery 86 can be charged from the primary power source while the chair is not used, by a battery charger 88 of a type for inserting a plug into a jack 87. At the center of the seat portion 80, there is provided a pressure switch 90 which is turned on when a person sits thereon. Switchable volume 89 provided at the rear side of the seat portion 80 is connected in series to the pressure switch. When the switchable volume 89 is turned on where the pressure switch 90 has been turned on by a sitting person thereon, the DC fan 83 is rotated. The revolution speed of this fan can be changed by rotating the switchable volume 89 to thereby adjust the blown air volume.

When a person sits on the cooling chair of this embodiment, the ambient air at a temperature lower than the body temperature is caused to flow such as just below the back and buttocks of the person to thereby increase the temperature gradient near the back and buttocks. Thus, even when the person keeps sitting for a long time, the portion of the cooling chair contacting the buttocks and back will be never warmed by the body temperature, resulting in comfortable feeling.

Embodiment 5

Figure 14:
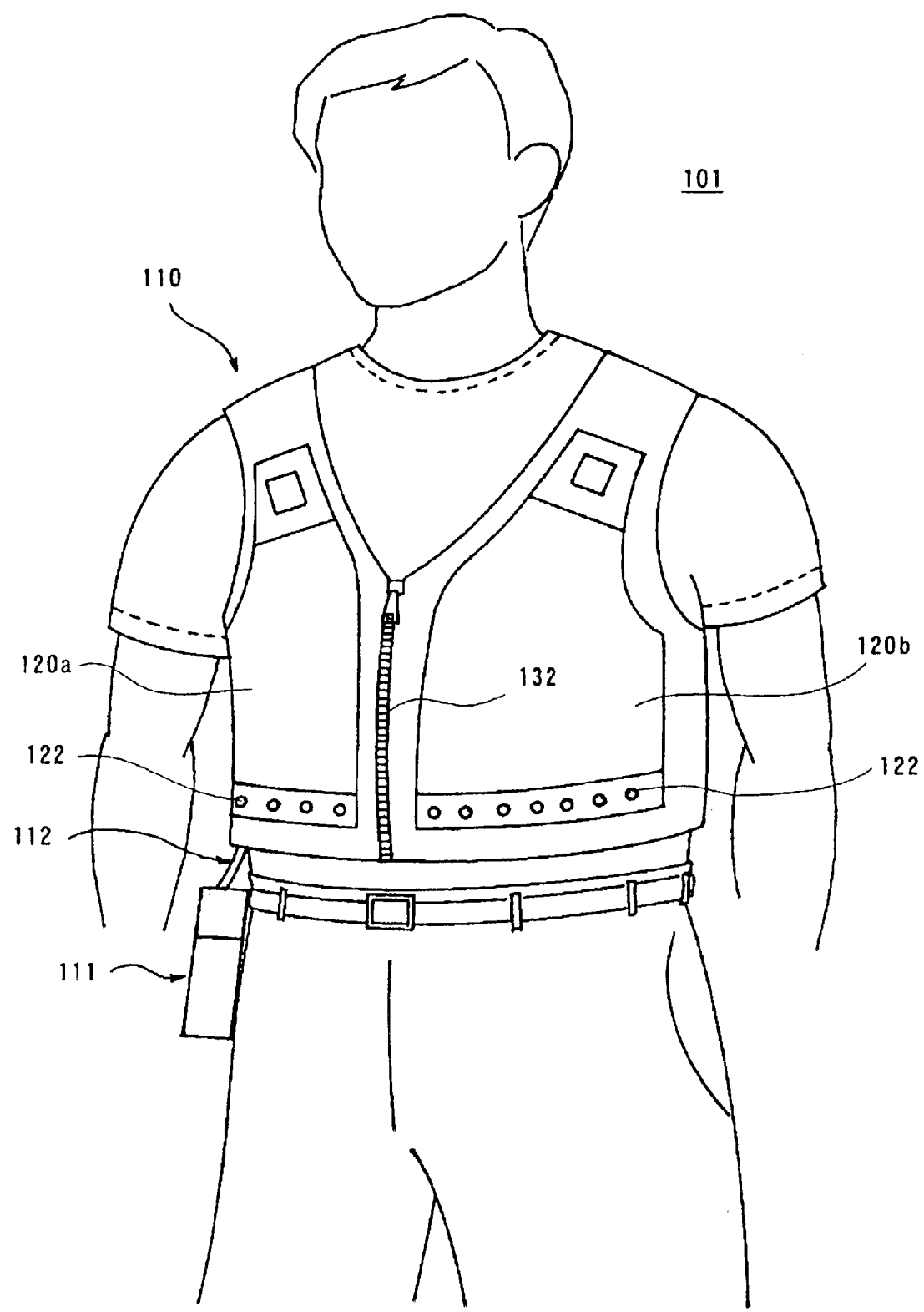
FIG. 14 is a perspective view of a piece of clothing in a worn state according to a fifth embodiment of the present invention applied to cooling clothing.

FIG. 14 is a perspective view of a piece of clothing in a worn state according to a fifth embodiment of the present invention applied to cooling clothes. As shown in FIG. 14, the cooling clothing 101 of this embodiment comprises a vest type main portion 110, and a controlling part 111 connected to the main portion 110 via cable 112. The main portion 110 can be worn in a manner similarly to a normal vest, such that a front fastener 132 of the main portion is opened, the arms of a person are sequentially passed through the sleeves, and then the fastener 132 is zipped up.

The main portion 110 is provided with front two and rear two pieces, totally four pieces, of cooling sheets 120a, 120b, 120c and 120d (rear cooling sheets 120c and 120d are omitted in the drawing). These cooling sheets are independent from one another. The provision of multiple cooling sheets is to facilitate the formation of the spacer. Should the whole of the clothing be formed of a single cooling sheet, it is difficult and impractical to form a flexible spacer well fitting to a body.

Those portions of the main portion 110 except the cooling sheets 120a through 120d are formed of an elastic fabric such as a material of polyurethane called Spandex. By sewingly connect this elastic fabric and four pieces of cooling sheets 120a through 120d, the cooling clothing 101 of the vest type is completed. In this case, the backsides of the cooling sheets 120 can be closely contacted with the wearer, by selecting a smaller size of the cooling clothing 101 so that the elastic fabric is slightly expanded upon wearing.

Each of the four pieces of cooling sheets 120a through 120d is provided with a DC fan 121 at the upper portion thereof and an air inlet 122 at the lower portion thereof. Further, a cooling flow passage is formed between the air inlet 122 and the DC fan 121. The DC fan 121 rotates in a direction to discharge air outwardly. Namely, rotation of the DC fan 121 causes air to be sucked via air inlet 122, to raise through the cooling flow passage, and then to be discharged by the DC fan 121. Each DC fan 121 is attached to the corresponding cooling sheet such as by a magic tape detachably. This allows the DC fan 121 to be readily removed such as upon washing the cooling clothes, resulting in convenience.

The controlling part 111 is provided with a battery 125 and a switchable volume 126. The battery 125 may be a normal dry cell or a rechargeable secondary battery. The role of the switchable volume 126 is identical with those in the aforementioned embodiments.

In this embodiment, the b-type of spacer is adopted as one for forming the cooling flow passage. This is because the spacer will not bear a larger load in case of clothes, so that a lighter one is advantageous. In this configuration, the b-type of planar spacer of FIGS. 4B1 and 4B2 is manufactured by injection molding a thermoplastic elastomer. By covering this spacer by an upper fabric, the cooling flow passage is formed. Thermoplastic elastomers have rubber-like characteristics after formation, thus have sufficient elasticity. In view of the consumption of the battery 125, the thickness of the cooling flow passage is limited to approximately 2 mm at the thinnest.

By wearing the cooling clothing 101 of this embodiment and turning on the switchable volume 126 to thereby rotate the DC fan 121, air is sucked into the air inlet 122 and raises through the cooling flow passage. At this time, an air layer having a temperature same with that of the ambient air is formed adjacently to the body surface, thereby increasing the temperature gradient adjacent to the body surface. Thus, even when the ambient temperature is on the order of 30° C., the wearer will feel coolness, resulting in comfortable feeling.

Embodiment 6

Figure 15:
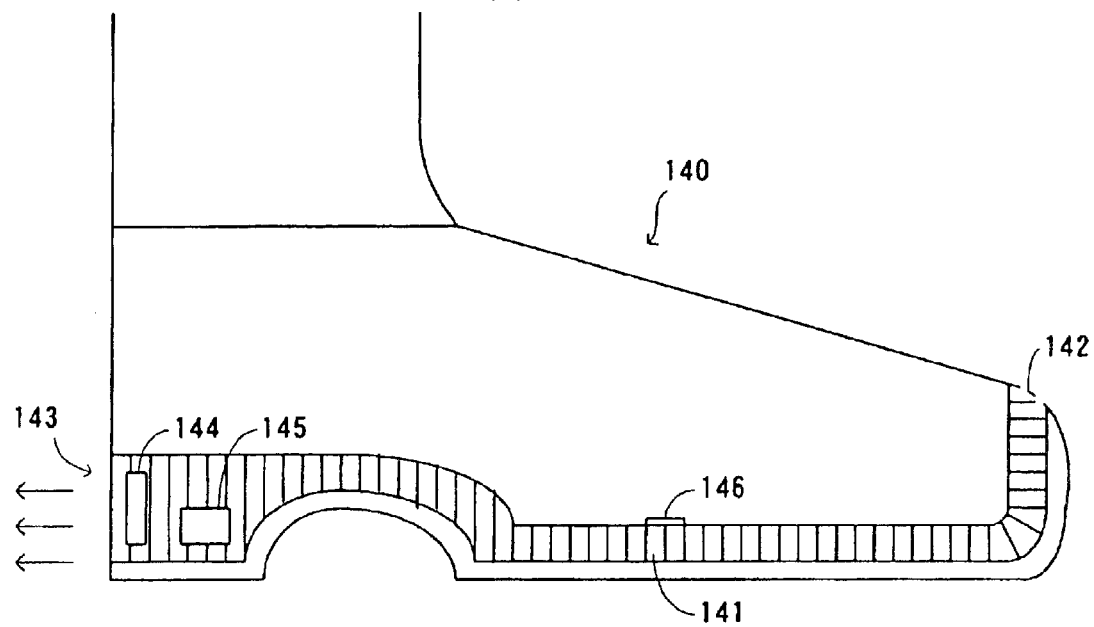
FIG. 15 is a cross-sectional view of one of a pair of shoes according to a sixth embodiment of the present invention applied to cooling shoes.

FIG. 15 is a cross-sectional view of one of a pair of shoes according to a sixth embodiment of the present invention applied to cooling shoes. As shown in FIG. 15, cooling shoe 140 of this embodiment is provided with a cooling flow passage 141 at the shoe bottom portion, an air inlet 142 at the toe portion, an air outlet 143 at the heel portion, and a DC fan 144 rotated in a direction for discharging air backwardly of the heel. At the heel portion, there is provided a battery 145 for energizing the DC fan 144. This battery 145 may be a normal dry cell or a rechargeable secondary battery.

The cooling shoe 140 of this embodiment is provided with a foot sensor 146 at a bottom portion within the shoe. This sensor constitutes a switch which is turned on by entrance of foot and turned off by withdrawal of foot. Thus, waste of power consumption during disuse of the shoe is avoided. As the foot sensor 146, such as a pressure switch may be adopted, but any other type of sensor may be adopted insofar as it can detect the used state of the shoe.

Wearing the cooling shoe 140 of this embodiment causes the foot sensor 146 to be turned on to thereby rotate the DC fan 144. Then, air is sucked through the air inlet 142, flows leftwardly through the cooling flow passage 141. At this time, an air layer having a temperature same with that of the ambient air is formed adjacently to the surface of the foot sole, thereby increasing the temperature gradient at this portion. Thus, even during midsummer, the interior of the shoes never become sweaty, thereby providing comfortable feeling.

Embodiment 7

Figure 16:
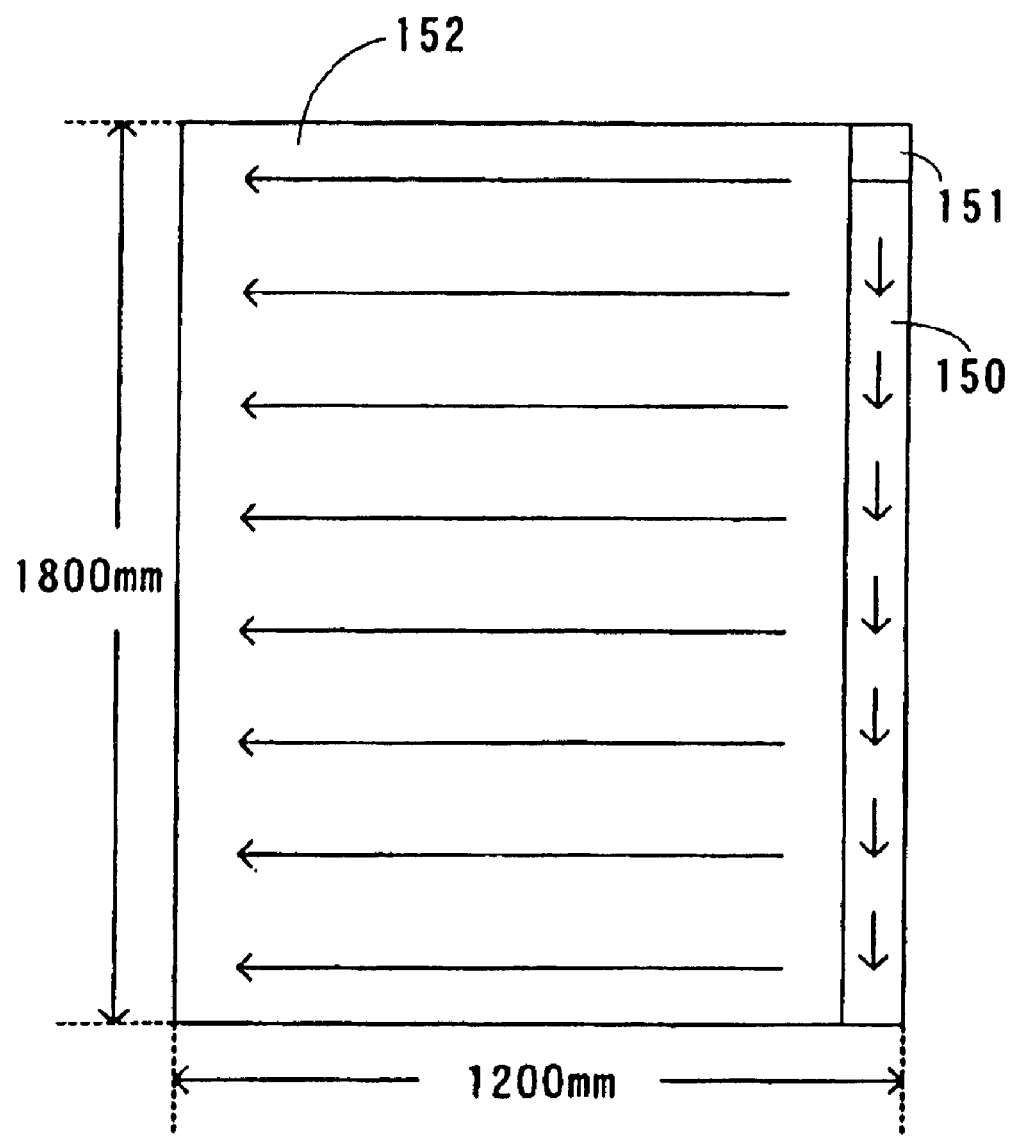
FIG. 16 is a plan view of a covering futon according to a seventh embodiment of the present invention applied to cooling bedclothes.
Figure 17:
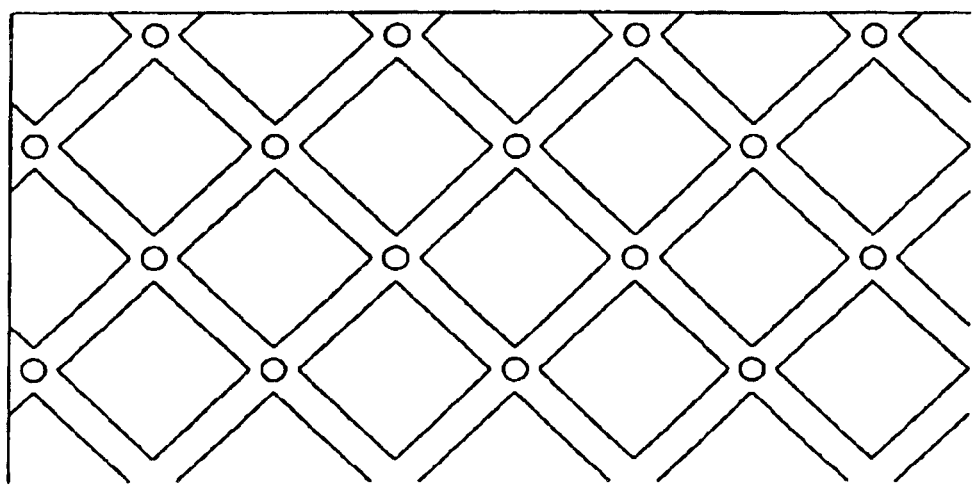
FIG. 17 is a view showing a structure of a spacer of the seventh embodiment.

FIG. 16 is a plan view of a covering futon according to a seventh embodiment of the present invention applied to cooling bedclothes, and FIG. 17 is a view showing a structure of a spacer of the seventh embodiment. As shown in FIG. 16, there are provided a flow connecting passage 150 at the right side of a supine person and an axial fan 151 of 60 square at the foot end of the passage 150. That side (right side of the supine person) of the cooling flow passage 152 which is provided with the flow connecting passage 150 acts as an air inlet, and the opposite side of the passage 152 acts as an air outlet. The fan 151 is arranged at the foot side of the lying person, in view of a noise problem. The total size of the cooling flow passage 152 and flow connecting passage 150 includes such as a length of 1,800 mm and a width of 1,200 mm.

As shown in FIG. 17, there is adopted a planar spacer obtained by slightly modifying the b-type one of FIGS. 4B1 and 4B2, as the planar spacer in this embodiment. This planar spacer is further lightened, by rectangular holes instead of circular ones. The cooling flow passage 152 is formed by covering the whole of the planar spacer by a bag-like fabric. The air drawn from the surroundings by the fan 151 into the cooling flow passage 152 flows laterally within the cooling flow passage 152, and finally exits from the outlet at the opposite side of the passage 152. In this way, an air layer having a temperature same with that of the ambient air is formed adjacently to the body surface to thereby increase the temperature gradient there, resulting in comfortable feeling even at a hot night.

As the bag-like fabric for forming the cooling flow passage 152, it is desirable to adopt the aforementioned high-density fabric. In this respect, even when the high-density fabric is adopted, its overall surface area is large so that excessively higher pressures at the portion just after the fan 151, i.e., at the flow connecting passage 150 lead to a problem of substantial leakage of air on its way. Further, excessively higher pressures also lead to a considerable noise problem. As such, the larger thickness of the cooling flow passage 152 is advantageous so as to ensure a sufficient blown air volume on the order of 5 liter/sec even at a lower pressure. For example, when the thickness of the cooling flow passage is on the order of 10 mm to 15 mm, there can be ensured a sufficient amount of blown air at a lower pressure. Only, the thickness of the cooling flow passage 152 may be reduced down to the order of 3 mm, such as when the blown air volume is reduced to a certain extent, the noise countermeasure for the fan 151 is enhanced, or a fabric having a higher thread density resistant to higher pressures is adopted. Even when the thickness of the cooling flow passage 152 is reduced in such a way, the pressure just after the fan 151 has a limit of 5 mmH$_2$O.

Also in this embodiment, it is desirable to provide a timer to avoid overcooling of a lying person. Such a timer may be arbitrarily used by the lying person, or may be arranged such that the fan is automatically stopped or the amount of blown air thereof is automatically reduced after an operation over a predetermined period of time of the fan.

Embodiment 8

Figure 18A:
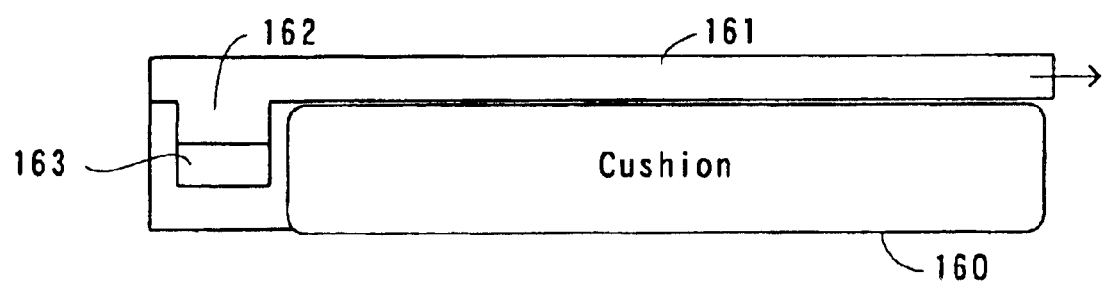
FIG. 18A and 18B are views showing a pillow according to an eighth embodiment of the present invention applied to cooling bedclothes.
Figure 18B:
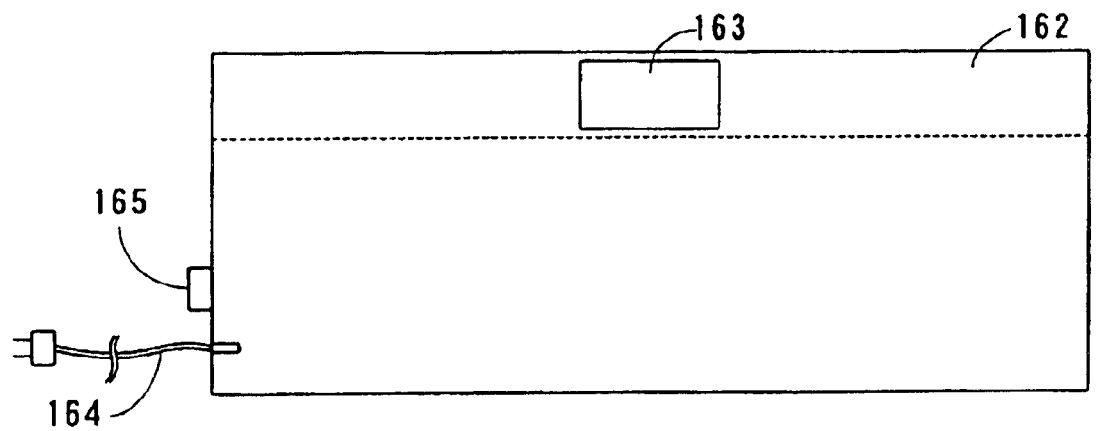

FIGS. 18A and 18B are views showing a pillow according to an eighth embodiment of the present invention applied to cooling bedclothes, wherein FIG. 18A is a cross-sectional view and FIG. 18B is a plan view thereof. Further, FIG. 19 is a cross-sectional view showing a sound-insulating countermeasure for a DC fan of the eighth embodiment.

The cooling bedclothes of this embodiment has a structure comprising a cooling flow passage 161 placed on a cushion 160. There is provided a flow connecting passage 162 at the upper portion of FIG. 18B (the left portion of FIG. 18A)), and a DC fan 163 of 50 square is provided at the center portion of the passage 162. This DC fan 163 is an axial fan, which rotates in a direction to suck air through the underside of the fan and feeds the air to the flow connecting passage 162 and cooling flow passage 161, and finally discharges the air at the opposite side of the passage 161.

In this embodiment, the d-type of planar spacer in FIGS. 4D1 and 4D2 is adopted as the spacer for forming the cooling flow passage 161. This planar spacer is manufactured by injection molding soft polyethylene.

As shown in FIG. 18B, there is provided a jack 164 for insertion of a DC adapter at the lateral portion of the pillow, and the DC fan 163 is supplied with power from the jack. Similarly, a switchable volume 165 is provided at the lateral portion of the pillow. The switchable volume 165 serves to turn on/off the operation of the fan, and to vary the rotational speed thereof to thereby adjust the blown air volume.

Figure 19A:
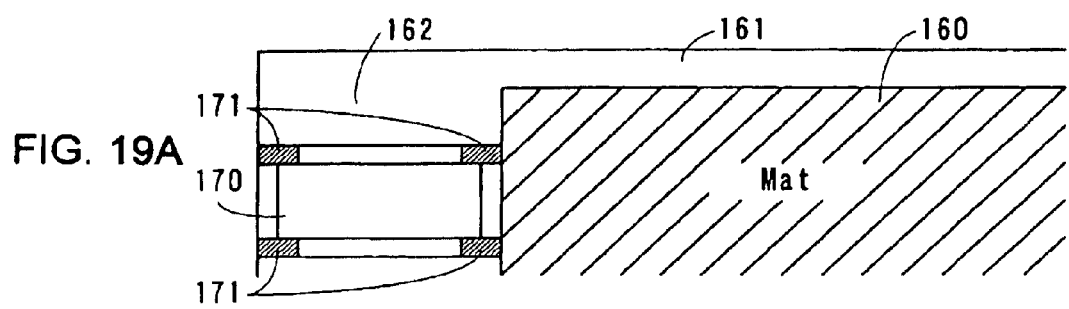
FIGS. 19A and 19B are cross-sectional views showing a sound-insulating countermeasure against a DC fan of the eighth embodiment.
Figure 19B:
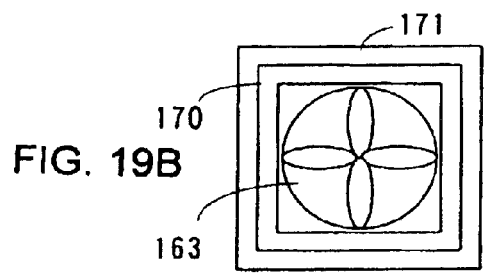

There will be described a noise countermeasure for the DC fan 163, with reference to FIGS. 19A and 19B. Since pillows are used during sleep, even a slight vibratory sound will hinder a calm sleep. Thus, it is critical to restrict the vibratory sound of the fan due to its rotation, down to a level which will never hinder a calm sleep. As such, in this embodiment, there is wound a weight 170 formed of metal such as iron around the DC fan 163 as shown in FIG. 17. In this way, the amplitude of any vibration is reduced. Further, the DC fan 163 wound with the weight 170 is fitted in the flow connecting passage 162 via gel-like absorbing material 171. This results in a state substantially free of noise even during the rotation of the DC fan 163.

When the pillow according to the cooling bedclothes of this embodiment is used to place thereon a head of a lying person and the switchable volume 165 is turned on, the DC fan 163 is rotated. This causes air to be sucked into the air inlet at the lower side of the DC fan 163, and to flow through the flow connecting passage 162 and cooling flow passage 161 rightwardly in FIG. 18A. At this time, an air layer having a temperature same with that of the ambient air is formed adjacently to the surface of the person's head, to thereby increase the temperature gradient at this portion. Thus, there is provided a calm sleep even during midsummer time.

According to the cooling bedclothes, cooling seat cushion, cooling mat, cooling chair, cooling clothing and cooling shoes of the present invention as described above, there is formed, at a location extremely adjacent to the body surface of a person, an air layer having a temperature equal to that in the room without lowering the temperature of the whole room, thereby forcibly increasing the temperature gradient near the body surface to thereby increase the extent of heat release from the body. Thus, any devices for cooling air are omitted to thereby reduce cost, without any uncomfortable feeling due to direct blowing of cooled air, thereby resulting in feeling of natural coolness.

Industrial Applicability

As described above, the present invention utilizes such a cooling effect to form the cooling flow passages in a substantially parallel and planar manner at the portion of an article adjacent to the body, and causes the ambient air at a temperature lower than the body temperature to flow through the cooling flow passages substantially patallel to the body surface to thereby cool the body. Thus, the present invention can be utilized in any articles such as bedclothes, mat, chair seat cushion, chair, clothing and shoes to which the cooling effect can be applied.

What is claimed is:

1. A cooling seat cushion usable on a seat portion, said cooling seat cushion comprising:

cooling flow passages formed in a substantially parallel and planar manner adjacent to a portion of said cooling seat cushion that contacts a body of a person, said cooling flow passages being formed from a spacer and a water-vapor permeable sheet-like material arranged between said spacer and said body;

an inlet for drawing air into said cooling flow passages;

an outlet for discharging the air from said cooling flow passages into the atmosphere;

an electromotive fan provided at at least one of said inlet and outlet;

a battery provided at a portion of said cooling seat cushion, for energizing said electromotive fan; and a flow connecting passage provided between said electromotive fan and said cooling flow passages, to thereby smoothly connect said electromotive fan and said cooling flow passages, said electromotive fan and cooling flow passages having different sizes;

whereby the ambient air at a temperature lower than the body temperature is caused by said electromotive fan to flow through said cooling flow passages substantially parallelly to the body surface so as to increase the temperature gradient between the body and said cooling flow passages in order to release the heat emitted from the body to thereby cool the body, and in order to discharge water vapor that has permeated through said sheet-like material into the atmosphere;

wherein said sheet-like material has a thickness of 5 mm or less;

wherein a static pressure caused by said electromotive fan is 5 mmH$_2$O or less; and wherein said spacer is formed from a common member and a plurality of physically contiguous subspacers formed on said common member integrally with the same, said subspacers being configured such that said cooling flow passages have a thickness of 2 mm to 30 mm.

2. The cooling seat cushion of claim 1, further comprising a pressure switch for sensing seating of the person and for actuating said electromotive fan upon detecting the seating of the person.

* * * * *